United States Patent [19]

Miyazaki et al.

[11] Patent Number: 5,385,880
[45] Date of Patent: Jan. 31, 1995

[54] PYRIDINE DERIVATIVE HERBICIDAL COMPOSITION CONTAINING THE SAME, AND METHOD FOR KILLING WEEDS

[75] Inventors: Masahiro Miyazaki; Masafumi Matsuzawa; Keiji Toriyabe, all of Shizuoka; Michiya Hirata, Kashiwa, all of Japan

[73] Assignees: Kumiai Chemical Industry Co., Ltd.; Ihara Chemical Industry Co., Ltd., both of Tokyo, Japan

[21] Appl. No.: 927,281

[22] PCT Filed: Mar. 26, 1992

[86] PCT No.: PCT/JP92/00362

§ 371 Date: Sep. 17, 1992

§ 102(e) Date: Sep. 17, 1992

[87] PCT Pub. No.: WO92/17468

PCT Pub. Date: Oct. 15, 1992

[30] Foreign Application Priority Data

Mar. 26, 1991 [JP] Japan .................. 3-084556

[51] Int. Cl.⁶ .......... C07D 239/34; C07D 239/60; C07D 401/12; A01N 43/54
[52] U.S. Cl. .......... 504/243; 504/242; 504/193; 544/229; 544/300; 544/310; 544/316; 544/317; 544/318; 544/320; 544/321; 544/324; 544/331
[58] Field of Search .......... 504/242, 243, 193; 544/300, 310, 316, 317, 318, 320, 321, 324, 331, 229

[56] References Cited

U.S. PATENT DOCUMENTS 5,015,285   5/1991   Rheinheimer et al. ........... 504/243
5,215,569   6/1993   Drewes et al. ................. 504/242

FOREIGN PATENT DOCUMENTS 467139    1/1992   European Pat. Off. .
3633485   4/1988   Germany .
414058    2/1991   Germany .
64-84     1/1989   Japan .
1-213202  8/1989   Japan .
1-290671  11/1989  Japan .
2-121973  5/1990   Japan .
2-216631  8/1990   Japan .

OTHER PUBLICATIONS

Heinemann et al., Chemical Abstracts, vol. 116, entry 128976d (1992).

*Primary Examiner*—John M. Ford
*Attorney, Agent, or Firm*—Oblon, Spivak, McClelland, Maier & Neustadt

[57] ABSTRACT

Herbicidal composition containing a compound having the following formula or its salt:

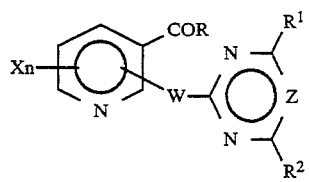

wherein W is an oxygen atom, a sulfur atom, a NH group or a group of the formula, >NC(O)B;
Z is a methine group or a nitrogen group;
X is a phenyl group which may be substituted or a group having the formula:

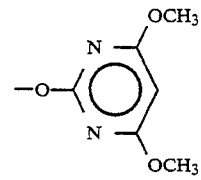

and n is an integer of from 1 to 3.

9 Claims, No Drawings

PYRIDINE DERIVATIVE HERBICIDAL COMPOSITION CONTAINING THE SAME, AND METHOD FOR KILLING WEEDS

INDUSTRIAL FIELD OF UTILIZATION

The present invention relates to a novel pyridine derivative and its salt, a method for preparing the same, a herbicidal composition containing the same as an effective ingredient, and a method for killing weeds.

PRIOR ART

Heretofore, as a pyridine carboxylic acid derivative having a herbicidal activity, there were known 3-(4,6-dimethoxypyrimidin-2-yl)oxypicolinic acid derivative (Japanese Unexamined Patent Publication No. 84/1989), pyrimidyloxypicolinic acid derivative and pyrimidyloxyisonicotinic acid derivative (japanese Unexamined Patent Publication No. 121973/1990 and 149567/1990).

However, these references do not describe a nicotinic acid derivative having a heterocyclic ring-containing substituent at the 2-position as in the contpound of the present invention.

Heretofore, many herbicides have been developed, and have contributed to the saving of energy for the agricultural operations and to the improvement of the production efficiency. However, in their practical use, such herbicides have various problems. For example, a herbicide achieving a herbicidal effect specially at a low dose is desired in view of environmental problems. Particularly, a desirable herbicide should have a herbicidal effect for killing perennial weeds such as johnsongrass (*Sorghum halepense*) and purple nutsedge (*Cyperus rotundus*) which are widely distributed on agricultural lands throughout the world and are hardly killed. Furthermore, a herbicide having a satisfactory selectivity and safety to crop plants is particularly desired in respect of agricultural management.

Up to now, the known compounds as described in the above references do not always have satisfactory herbicidal effects.

The present inventors have conducted extensive research on nicotinic acid derivatives with an aim to develop a compound having a satisfactory herbicidal activity, and as a result, have found that the pyridine derivative of the present invention which is a nicotinic acid derivative having a heterocyclic ring-containing substituent at the 2-position, has an excellent herbicidal activity for killing annual and perennial weeds including gramineous weeds, cyperaceous weeds and broadleaf weeds by water treatment of rice fields and soil treatment or foliage treatment of upland fields, and also has a satisfactory safety to crop plants including rice, wheat and the like. The present invention has been accompanished on the basis of this discovery.

DISCLOSURE OF THE INVENTION

The pyridine derivative of the present invention is defined by the general formula (I):

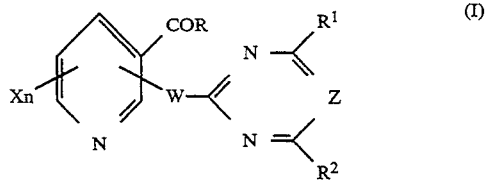

wherein R is a hydrogen atom, a hydroxyl group, an alkoxy group, an alkoxyalkoxy group, an acyloxyalkoxy group, a benzyloxy group which may be substituted, a trimethylsilylethoxy group, an alkylsulfonylamino group, an alkylthio group, a phenoxy group which may be substituted, a thiophenoxy group which may be substituted or an imidazolyl group;

$R^1$ and $R^2$ are the same or different, and are a hydrogen atom, an alkoxy group, a halogen atom, an alkylamino group, a dialkylamino group, a haloalkoxy group or an alkyl group;

X is a halogen atom, a halogen-substituted alkyl group, an acylamino group, an alkyl group, a cycloalkyl group, a haloalkyl group, an alkenyloxy group, an alkynyloxy group, an alkoxycarbonyl group, an alkoxy group, an alkylamino group, a dialkylamino group, a phenyl group, a substituted phenyl group, a benzyloxy group which may be substituted, a benzylthio group which may be substituted, a benzyl group which may be substituted, a phenoxy group which may be substituted, a thiophenoxy group which may be substituted, an alkoxyiminoalkyl group, an acyl group, an alkylthio group, an arylamino group which may be substituted or a group having the formula,

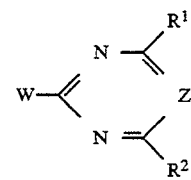

W is an oxygen atom, a sulfur atom, a NH group or a group of the formula, >NCOB (wherein B is a hydrogen atom or an alkoxy group);

Z is a methine group or a nitrogen atom; and n is 0 or an integer of 1 to 3, and X may be a combination of different groups when n is at least 2.

The present invention relates to a pyridine derivative and its salt.

Also, the present invention further relates to a method for preparing the pyridine derivative, a herbicidal composition containing the pyridine derivative or its salt as an effective ingredient and a method for killing weeds.

In the general formula (I), examples of the alkoxy group of R include a straight-chain or branched $C_1$–$C_7$ alkoxy group such as a methoxy group, an ethoxy group, a n-propoxy group, an isopropoxy group, a n-butoxy group, an isobutoxy group, a s-butoxy group, a t-butoxy group, a n-pentyloxy group, an isopentyloxy group, a s-pentyloxy group, a t-pentyloxy group, a n-hexyloxy group, a 2,2-dimethylpropyl group, a 2-methylbutoxy group, a 2-ethylbutoxy group, a 3,3- dimethylbutoxy group, and a 1,3,3-trimethylbutoxy group.

Examples of the alkoxy group of $R^1$ and $R^2$ are as defined in the above alkoxy group of R. Examples of the halogen atom include chlorine, bromine, fluorine and iodine. Examples of the alkylamino group include a straight-chain or branched $C_1$–$C_3$ alkylamino group such as a methylamino group, an ethylamino group, a n-propylamino group and an isopropylamino group. Examples of the dialkylamino group include a straight-chain or branched $C_1$–$C_3$ dialkylamino group such as a dimethylamino group, a diethylamino group, a methylethylamino group, a di-n-propylamino group and a diisopropylamino group. Examples of the haloalkoxy group include a straight-chain or branched $C_1$–$C_7$ haloalkoxy group having a part or the whole part of the alkoxy group substituted with the above-mentioned halogen atoms, such as a difluoromethoxy group and a chloromethoxy group. Examples of the alkyl group include a straight-chain or branched $C_1$–$C_7$ alkyl group such as a methyl group, an ethyl group, n-propyl group, an isopropyl group, a n-butyl group, an isobutyl group, a s-butyl group, a t-butyl group, a n-pentyl group, an isopentyl group, a s-pentyl group, a t-pentyl group, a n-hexyl group, a 2,2-dimethylpropyl group, a 2-methylbutyl group, a 2-ethylbutyl group, a 3,3-dimethylbutyl group and a 1,3,3-trimethylbutyl group.

Examples of the halogen atom, alkylamino group and dialkylamino group of X are as defined in the above-mentioned halogen atom, alkylamino group and dialkylamino group of $R^1$ and $R^2$. Examples of the halogen-substituted alkyl group include a halogen-substituted alkyl group having a part or the whole part of a straight-chain or branched $C_1$–$C_3$ alkyl group substituted with the above-mentioned halogen atoms, such as a difluoromethyl group, a chloromethyl group and a tribromomethyl group. Examples of the alkyl group are as defined in the above-mentioned alkyl group of $R^1$ and $R^2$. Examples of the alkoxy group are as defined in the above-mentioned alkoxy group of $R^1$ and $R^2$.

Examples of the haloalkoxy group are as defined in the above-mentioned haloalkoxy group of $R^1$ and $R^2$.

Examples of the cycloalkyl group include a $C_3$–$C_7$ cycloalkyl group such as a cyclopropyl group, a cyclopentyl group and a cyclohexyl group.

Examples of the alkenyloxy and alkynyloxy groups include $C_2$–$C_8$ alkenyloxy and alkynyloxy groups.

Examples of the substituted phenyl group include a substituted phenyl group, a part or the whole part of the phenyl group being substituted with the above-mentioned halogen, lower alkyl, lower alkoxy, alkylamino, dialkylamino, halogen-substituted alkyl, haloalkoxy, nitro, hydroxy, alkoxyalkoxy, alkoxycarbonylalkoxy, alkylthioalkoxy, benzyloxy, cyano, phenoxy, substituted phenoxy, alkylthio, alkoxyalkyl or ethynyl group, such as a p-chlorophenyl group and a 3-tolyl group.

Examples of a preferable compound include a compound of the general formula (I) wherein R is a hydroxyl group, a methoxy group, an ethoxy group, a benzyloxy group, an ethoxymethoxy group, a pivaloyloxymethoxy group or a trimethylsilylethoxy group; $R^1$ and $R^2$ are the same or different and are a hydrogen atom, a chlorine atom, a methyl group, a methoxy group, a dimethylamino group or a halogen-substituted methoxy group; X is a hydrogen atom, a chlorine atom, a bromine atom, a methyl group, a halogen-substituted methyl group, a phenyl group, a halogen-substituted phenyl group, a methyl-substituted phenyl group, a methoxy-substituted phenyl group or a mono or dimethylamino group; W is an oxygen atom, a sulfur atom, a NH group or an acylamino group; Z is a methine group or a nitrogen atom; and n is 0 or an integer of 1 to 3.

The compound of the present invention of the general formula (I) can be prepared, for example, by the following preparation method, but the present invention is not limited to these methods.

PREPARATION METHOD 1

Reaction formula 1

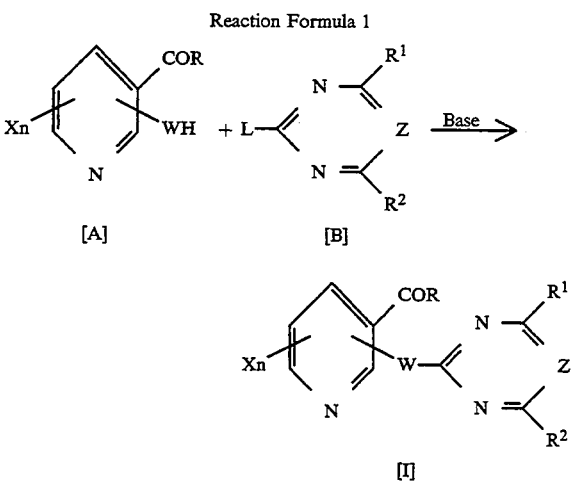

(wherein L is a halogen atom, an alkylsulfonyl group, a benzylsulfonyl group which may be substituted, an alkylsulfonate group, a haloalkylsulfonate group and a benzylsulfonate group which may be substituted; and W, X, n, R, $R^1$, $R^2$ and Z are as defined above.)

The compound of the general formula (I) can be prepared by reacting a compound of the formula (A), with a compound of the formula (B) in the presence of a base having an amount of at least equivalent amount in an appropriate solvent at a temperature ranging from room temperature to the boiling point of the solvent for from 0.5 to 24 hours.

Examples of the base include alkali metals such as metallic lithium, metallic sodium and metallic potassium; organic lithium reagents such as n-butyl lithium and lithium diisopropylamide (LDA); hydrogenated alkali metals and hydrogenated alkali earth metals such as hydrogenated sodium, hydrogenated potassium and hydrogenated calcium; alkali metal alkoxides such as potassium t-butoxide; alkali metal carbonates such as sodium carbonate and potassium carbonate; and alkali metal hydroxides such as sodium hydroxide and potassium hydroxide.

Examples of the solvent include hydrocarbon type solvents such as hexane, benzene, toluene and xylene; halogenated hydrocarbon type solvents such as dichloromethane and chloroform; ether type solvents such as diethyl ether, tetrahydrofuran and 1,4-dioxane; ester type solvents such as methyl acetate and ethyl acetate; ketone type solvents such as acetone and methyl ethyl ketone; aprotic polar solvents such as N,N-dimethlformamide, N,N-dimethylacetamide and diemthylsulfoxide; and acetonitrile, etc.

The compound of the formula (A) can be prepared in the accordance with the methods disclosed in "Journal of Medicinal Chemistry" (vol. 6, p. 294, 1963; and vol.

7, p. 17, 1964), "Berichte" (74B, p. 1111, 1941), "Liebigs Ann. Chem." (371, 1979) and the like, but can also be prepared by the following method.

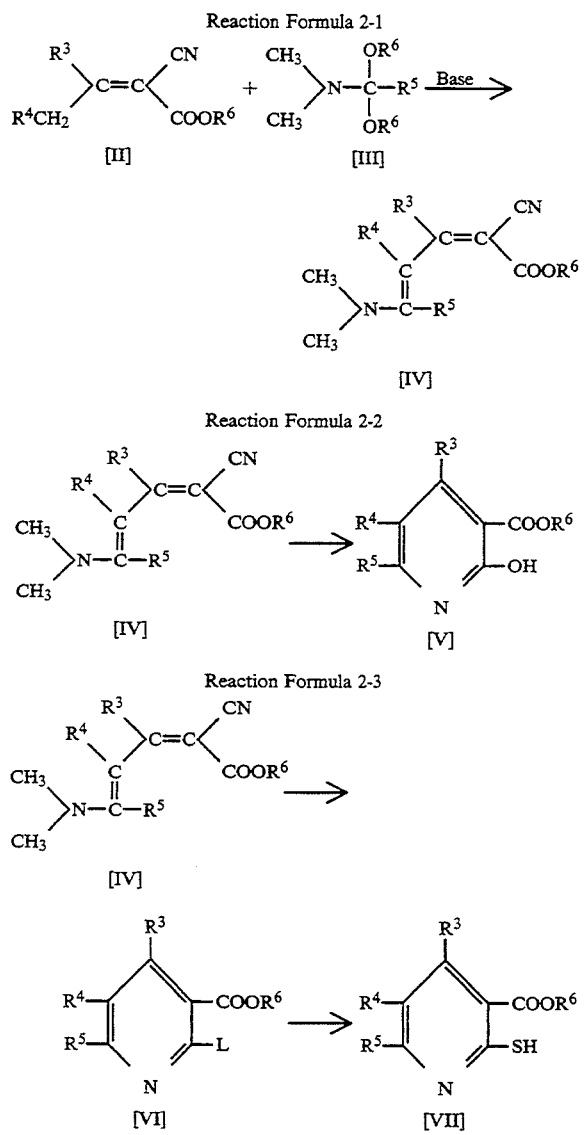

(wherein $R^3$, $R^4$ and are the same or different, and are $R^5$ are the same or different, and are a hydrogen atom, a lower alkyl group, a lower alkoxy group, an alkylamino group, a dialkylamino group, a phenyl group or a substituted phenyl group; and $R^6$ is an alkyl group.)

The compound of the formula (IV) can be prepared by heating a compound of the formula (II) and an acetal compound of the formula (III) in the presence or absence of an inorganic or organic base for from 0.1 to 10 hours in an appropriate solvent including alcohols such as methanol and ethanol, ethers such as tetrahydrofuran, aprotic polar solvents such as N,N-dimethylformamide or acetonitrile ("Archiv der Pharmazie" vol. 318, p. 481, 1985).

The compound of the formula (V) can be prepared by further reacting the above prepared compound of the formula (IV) at room temperature for from 1 hour to 7 days in an acid such as polyphosphoric acid, aqueous hydrogen halide, sulfuric acid and acetic acid.

Also, the compound of the formula (VI) can be prepared by reacting the compound of the formula (IV) with hydrogen bromide or hydrogen chloride gas in an inert solvent such as dichloroethane and toluene or acetic acid at a temperature ranging from 0° C. to the boiling point of the solvent, preferably from 10° C. to 50° C.

Furthermore, the compound of the formula (VII) can be prepared by reacting the above prepared compound of the formula (VI) with thiourea at 50° C. to 120° C. for 0.5 to 10 hours in the presence of water and a mineral acid such as hydrochloric acid and sulfuric acid, treating the resultant product with an alkaline material such as sodium hydroxide and potassium hydroxide, and then acidifying the resultant product with an acid such as hydrochloric acid (see Japanese Unexamined Patent Publication No. 275562/1989). The product thus obtained contains a small amount of sulfide and disulfide in addition to the aimed thiol compound.

PREPARATION METHOD 2

Reaction Formula 3

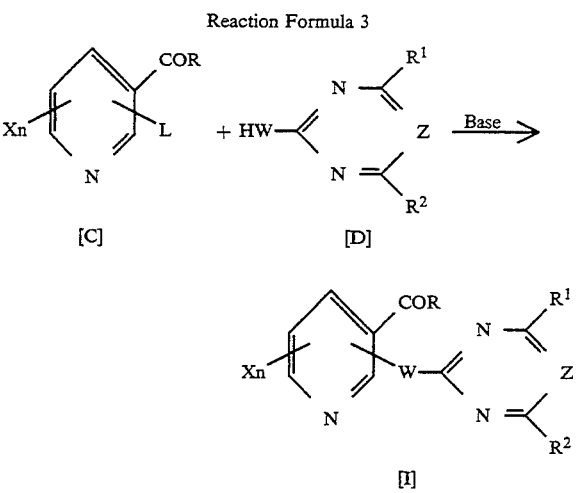

(wherein L, X, n, R, $R^1$, $R^2$, Z and W are as defined above.)

The compound of the formula (I) can also be prepared by reacting a compound of the formula (C) with a compound of the formula (D) in the presence of a base having an amount of at least equivalent amount in an appropriate solvent for 0.5 to 24 hours at a temperature ranging from room temperature to the boiling point of the solvent. The base and the solvent used may be the same in the above Preparation Method 1.

PREPARATION METHOD 3

Reaction Formula 4

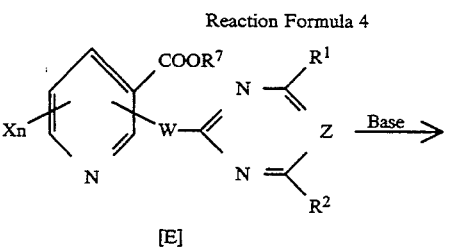

-continued

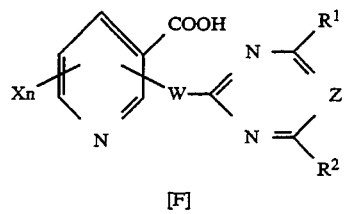

[F]

(wherein $R^7$ is an alkyl group or a trimethylsilylethyl group; and X, n, W, Z, $R^1$ and $R^2$ are as defined above.)

The compound of the formula (F) can be prepared by reacting the compound of the formula (E) in the presence of a base having an amount of at least equivalent amount in an appropriate solvent such as water or a solvent containing water for 0.5 to 24 hours at a temperature of from room temperature to the boiling point of the solvent and then acidifying the resultant product.

Examples of the base include alkali metal hydroxides such as sodium hydroxide and potassium hydroxide; alkali metal carbonates such as sodium carbonate and potassium carbonate; and alkali metal hydrogen carbonates such as sodium hydrogen carbonate and potassium hydrogen carbonate. In the case of trimethylsilyl ethyl ester, examples of the base used include tetrabutylammonium fluoride and potassium fluoride.

Examples of the solvent include hydrocarbon type solvents such as hexane; halogenated hydrocarbon type solvents such as dichloromethane and chloroform; alcohol type solvents such as methanol, ethanol and 2-propanol; ether type solvents such as ethyl ether, tetrahydrofuran and 1,4-dioxane; ketone type solvents such as acetone and methyl ethyl ketone; aprotic polar solvents such as N,N-dimethylformamide, N,N-dimethylacetamide and dimethylsulfoxide; and acetonitrile or the like.

PREPARATION METHOD 4

Reaction Formula 5

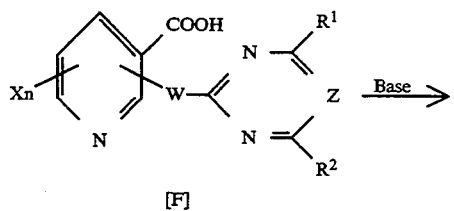

[F]

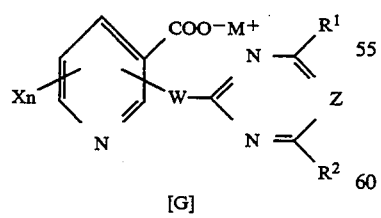

[G]

(wherein $M^+$ is 1 equivalent amount of alkali metal, alkali earth metal, ammonium or organic ammonium ion; and X, n, W, Z, $R^1$ and $R^2$ are as defined above.)

The compound of the formula (G) can be prepared by reacting the compound of the formula (F) with an equivalent amount of a base in an appropriate solvent for 0.5 to 24 hours at a temperature ranging from room temperature to the boiling point of the solvent.

Examples of the base include hydrogenated alkali metals such as sodium hydride and potassium hydride; alkali metal alkoxides such as sodium methylate and sodium ethylate; alkali metal hydroxides and alkali earth metal hydroxides such as sodium hydroxide and calcium hydroxide; alkali metal carbonates and alkali earth metal carbonates such as sodium carbonate and calcium carbonate; alkali metal hydroxides and alkali earth metal hydroxides such as sodium hydroxide, potassium hydroxide and calcium hydroxide; alkali metal hydrogencarbonates such as sodium hydrogencarbonate and potassium hydrogencarbonate; and organic amines such as ammonia and isopropylamine.

Examples of the solvent include hydrocarbon type solvents such as benzene, toluene and xylene; halogenated hydrocarbon type solvent such as dichloromethane and chloroform; alcohol type solvents such as methanol, ethanol and 2-propanol; ether type solvents such as diethyl ether, tetrahydrofuran and dioxane; aprotic polar solvents such as N,N-dimethylacetamide and dimethylsulfoxide; and acetonitrile, water or the like.

PREPARATION METHOD 5

Reaction Formula 6

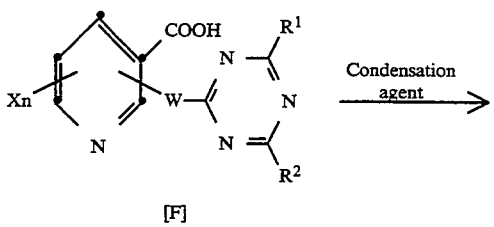

[F]

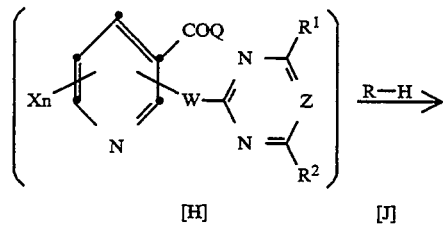

[H]    [J]

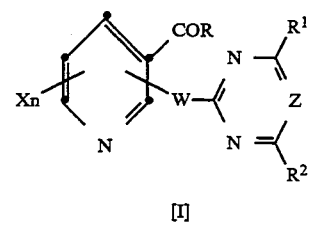

[I]

(wherein Q is a halogen atom, a cyano group, an imidazolyl group or a substituted amidinoxy group; and R, $R^1$, $R^2$, X, n, W and Z are as defined above.)

The intermediate compound of the formula (H) for preparing the compound of the present invention of the formula (I) can be prepared by reacting the compound of the formula (F) with a condensation agent having an amount of at least equivalent amount in an appropriate solvent for 0.5 to 24 hours at a temperature ranging from −10° C. to the boiling point of the solvent. The intermediate compound thus prepared may be separated or may not be separated, and the compound of the formula (I) can be prepared by reacting the intermediate compound with a compound of the formula (J) and a base having an amount of at least equivalent amount in an appropriate solvent for 0.5 to 24 hours at a temperature ranging from −10° C. to the boiling point of the solvent.

Examples of the condensation agent include thionyl chloride, oxalic acid dichloride, chlorocarbonic acid ester, carbonyldiimidazole, cyanophosphoric acid ester, carbodiimide and the like. Examples of the base and the solvent used are as defined in the above Preparation Method 1.

PREPARATION METHOD 6

Reaction Formula 7

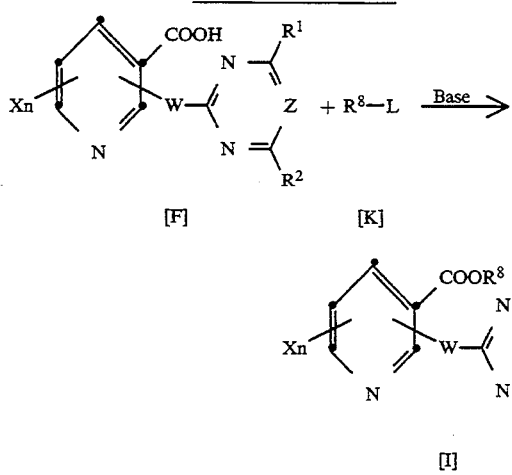

[F]   [K]

[I]

(wherein $R^8$ is an alkyl group, an alkoxyalkyl group, an acyloxyalkyl group or a benzyl group which may be substituted; and $R^1$, $R^2$, L, W, X, n and Z are as defined above.)

The compound of the formula (I) can be prepared by reacting the compound of the formula (F) with the compound of the formula (K) in the presence of a base having an amount of at least equivalent amount in an appropriate solvent for 0.5 to 24 hours at a temperature ranging from −10° C. to the boiling point of the solvent. Examples of the base and the solvent used are as defined in the above Preparation Method 1.

BEST MODE FOR CARRYING OUT THE INVENTION

In the following, the method for preparing the compound of the present invention is more concretely explained by giving Examples.

Preparation Example 1

Synthesis of methyl 2-(4,6-dimethoxypyrimidin-2-yloxy)-4-phenylnicotinate (Compound No. 18)

50.0 g (0.22 mol) of methyl 2-hydroxy-4-phenylnicotinate and 200 ml of dichloromethane were weighed and added dropwise to 50.0 g (0.24 mol) of trifluoromethane sulfonic anhydride at around −20° C. After the dropwise addition, the resultant mixture was further stirred at a temperature of from −20° C. to −10° C. for 30 minutes, and thereafter the temperature was restored to room temperature. The reaction mixture was then poured into water and was extracted with 300 ml of dichloromethane, and the organic layer was then washed with water and a saturated sodium chloride aqueous solution. After drying, the solvent was distilled off to obtain 50.0 g of a yellow viscous liquid of methyl 2-methanesulfonyl-4-phenylnicotinate (yield=64%).

Thereafter, 25.0 g (0.16 mol) of 4,6-dimethoxy-2-hydroxypyrimidine, 25.0 g (0.18 mol) of potassium carbonate and 200 ml of dimethylsulfoxide were weighed, and were heated at 80° C. for 30 minutes. After cooling the resultant mixture to room temperature, 50.0 g (0.14 mol) of the above synthesized sulfonate was added thereto and the resultant mixture was reacted at 90° C. for 2 hours. The reaction mixture was poured into water, and was extracted with 300 ml of ethyl acetate. Thereafter, the organic layer was washed with water and a saturated sodium chloride aqueous solution, and was dried with anhydrous sodium sulfate. The solvent was then distilled off, and the residue was purified by silica gel column chromatography to obtain 3.6 g of the aimed product.

Yield: 4.5%, Melting point: 111°°–115° C.

Preparation Example 2

Synthesis of 2-(4,6-dimethoxypyrimidin-2-yloxy)-4-phenylnicotinic acid (Compound No. 7)

2.6 g (0.007 mol) of methyl 2-(4,6-dimethoxypyrimidin-2-yloxy)-4-phenylnicotinate and 50 ml of dimethylsulfoxide were weighed, and 4.6 ml (0.009 mol) of 2N sodium hydroxide aqueous solution was added dropwise thereto at 60° C. After the dropwise addition, the resultant mixture was further stirred for 30 minutes at 60° C. The resultant mixture was poured into water, and was washed twice with ethyl acetate. The aqueous layer was then adjusted to pH 2 with 10% hydrochloric acid aqueous solution, and the precipitated crystal was filtrated out. The crystal thus obtained was washed with water, and was then dried. The dried crystal was recrystallized with ethyl acetate to obtain 1.1 g of a white crystal.

Yield: 44%, Melting point: 165°–169° C.

PREPARATION EXAMPLE 3

Synthesis of methyl 2-(4,6-dimethoxypyrimidin-2-yloxy)-6-methylnicotinate (Compound No. 11)

5.0 g (0.03 mol) of methyl 2-hydroxy-6-methylnicotinate, 5.0 g (0.03 mol) of potassium carbonate, 5.7 g (0.03 mol) of 2-chloro-4,6-dimethoxypyrimidine and 50 ml of N,N-dimethylformamide were weighed, and were reacted at 100° C. for 4 hours. The reaction mixture was then poured into water, and was extracted with 100 ml of ethyl acetate. The organic layer was then washed with water and a saturated sodium chloride aqueous solution. After drying with anhydrous sodium sulfate, the solvent was distilled off, and the residue was purified by silica gel column chromatography to obtain 0.73 g of the aimed product.

Yield: 8.0%, Melting point: 99°–103° C.

PREPARATION EXAMPLE 4

Synthesis of potassium 2-(4,6-dimethoxypyrimidin-2-yloxy)-4,6-dimethylnicotinate (Compound No. 2)

1.5 g (0.005 mol) of 2-(4,6-dimethoxypyrimidin-2-yloxy)-4,6-dimethylnicotic acid, 0.49 g (0.005 mol) of potassium hydrogencarbonate, 10 ml of acetone and 10 ml of water were weighed, and were stirred at room temperature for 1 hour and further at 50° C. for 20 minutes. The solvent was distilled off under reduced pressure, and 10 ml of ethyl acetate was added to the residue. The crystal thus precipitated was filtrated out, and was dried to obtain 1.6 g of the aimed product.

Yield: 95%, Melting point: 188°–195° C.

PREPARATION EXAMPLE 5

Synthesis of 4-(4,6-dimethoxypyrimidin-2-yloxy)-2-phenyl-6-methylnicotinic acid (Compound No. 4)

2.0 g (0.004 mol) of 2-trimethylsilylethyl 4-(4,6-dimethoxypyrimidin-2-yloxy)-2-phenyl-6-methylnicotinate was dissolved in 30 ml of tetrahydrofuran, and 12 ml of 1 mol aqueous solution of tetrabutylammonium fluoride was added thereto. The resultant mixture was stirred at room temperature for one night. The reaction mixture was then poured into 200 ml of water, and 1.5 ml of concentrated hydrochloric acid was added thereto. The resultant reaction mixture was extracted with ethyl acetate, and was washed with water. The resultant reaction mixture was then dried with magnesium sulfate, and the solvent was distilled off to obtain 0.9 g of the aimed product.

Yield: 60%, Melting point: 277°–284° C.

PREPARATION EXAMPLE 6

Synthesis of methyl 4-(4-chlorophenyl)-2-(4,6-dimethoxypyrimidin-2-ylthio)nicotinate (Compound No. 93)

73.9 g (0.24 mol) of 2-bromo-4-(4-clorophenyl)nicotinic acid and 22.0 g (0.29 mol) of thiourea were weighed, and 100 ml of 5% HCl aqueous solution and 150 ml of acetic acid were added thereto. The resultant mixture was stirred at 100° C. for 2 hours, and was poured into water. Thereafter, 400 ml of 50% sodium hydroxide aqueous solution was added to the resultant mixture, and the mixture was stirred at room temperature for 30 minutes. The mixture was then acidified with 20% HCl aqueous solution, and the crystal thus precipitated was filtrated out and was washed with water. The washed crystal was then dried to obtain a crude crystal of 2-mercapto-4-(4-chlorophenyl)nicotinic acid.

The crude crystal thus obtained, 66.0 g (0.30 mol) of 4,6-dimethoxy-2-methylsulfonylpyrimidine and 104.0 g (0.75 mol) of potassium carbonate were weighed, and 500 ml of dimethylsulfoxide was added thereto. The resultant mixture was stirred at 80° C. for 2 hours. After the temperature was restored to room temperature, 68.0 g (0.48 mol) of methyl iodide was added to the reaction mixture, and the resultant reaction mixture was stirred at room temperature for 30 minutes. The reaction mixture was then poured into water, and was extracted with 1 l of ethyl acetate. After washing with water and a saturated sodium chloride aqueous solution, it was dried with anhydrous sodium sulfate. After filtration, the solvent was distilled off, and the residue was purified by silica gel column chromatography (developing solvent: ethyl acetate/hexane=¼) to obtain 19.0 g of a white crystal of the aimed product.

Yield: 19.2%, Melting point: 138°–141.5° C.

PREPARATION EXAMPLE 7

Synthesis of 4-(chloroophenyl)-2-(4,6-dimethoxypyrimidin-2-ylthio)nicotinic acid (Compound No. 94)

16.8 g (0.040 mol) of methyl 4-(4-chlorophenyl)-2-(4,6-dimethoxypyrimidin-2-ylthio)nicotinate and 150 ml of dimethylsulfoxide were weighed, and 35 ml (0.070 mol) of 2N sodium hydroxide aqueous solution was dropwise added thereto at 60° C. After the dropwise addition, the resultant mixture was stirred at 60° C. for 30 minutes. The mixture was then poured into water, and was washed twice with ethyl acetate. The aqueous layer thus obtained was acidified with 10% hydrochloric acid aqueous solution, and was extracted with 500 ml of ethyl acetate. After washing with water and a saturated sodium chloride aqueous solution, it was dried with anhydrous sodium sulfate. After filtration, the solvent was distilled off, and the remained crystal was washed with methanol and isopropyl ether to obtain 11.5 g of a white crystal of the aimed product.

Yield: 70.8%, Melting point: 219°–223° C.

PREPARATION EXAMPLE 8

Synthesis of pivaloyloxymethyl 4-(4-fluorophenyl)-2-(4,6-dimethoxypyrimidin-2-ylthio)nicotinate (Compound No. 106)

0.70 g (0.0019 mol) of 4-(4-fluorophenyl)-2-(4,6-dimethoxypyrimidin-2-ylthio)nicotinic acid and 0.50 g (0.0036 mol) of potassium carbonate were weighed, and 10 ml of dimethylformamide was added thereto. The mixture was then stirred at room temperature for 1 hour. Thereafter, 0.34 g (0.0022 mol) of chloromethyl pivalate was further added to the resultant mixture, and the mixture was stirred at room temperature for 2 hours. The mixture was then poured into water, and was extracted with 50 ml of ethyl acetate. After washing with water and a saturated sodium chloride aqueous solution, it was dried with anhydrous sodium sulfate. After filtration, the solvent was distilled off, and the residue was purified by silica gel chromatography (developing solvent: ethyl acetate/hexane=¼) to obtain 0.81 g of a yellowish thick syrup-like aimed product.

Yield: 88.0%, Refractive index ($n_{D20}$): 1.5615

PREPARATION EXAMPLE 9

Synthesis of methyl 4-(4-isopropopoxyphenyl)2-(4,6-dimethylpyrimidin-2-ylthio)nicotinate (Compound No. 180)

20.0 g (0.059 mol) of 2-bromo-4-(4-isopropoxyphenyl)nicotinic acid and 5.5 g (0.072 mol) of thiourea were weighed, and 40 ml of 5% HCl aqueous solution and 60 ml of acetic acid were added thereto. The resultant mixture was stirred at 100° C. for 2 hours. After pouring the reaction mixture into water, 200 ml of 50% sodium hydroxide aqueous solution was added thereto, and the mixture was stirred at room temperature for 30 minutes. The mixture was then acidified with 20% HCl to precipitate a crystal, and the precipitated crystal was washed with water and then dried. Thereafter, the above synthesized crude crystal of thiosalicylic acid, 11.1 g (0.060 mol) of 4,6-dimethyl-2-methylsulfonylpyrimidine, and 25.0 g (0.18 mol) of potassium carbonate were weighed, and 200 ml of dimethylsulfoxide was added thereto and the resultant mixture was stirred at 80° C. for 2 hours. After restoring the temperature to room temperature, 16.8 g (0.12 mol) of methyl iodide was added to the reaction mixture, and the mixture was stirred at room temperature for 30 minutes. The reaction mixture was then poured into water, and was extracted with 500 ml of ethyl acetate. After washing with water and a saturated sodium chloride aqueous solution, it was dried with anhydrous sodium sulfate. After filtration, the solvent was distilled off, and the residue was purified by silica gel column chromatography (developing solvent: ethyl acetate/hexane=½) to obtain 6.5 g of a light-yellowish thick syrup-like aimed product.

Yield: 26.7% Refractive index ($n_{D20}$): 1.5965

PREPARATION EXAMPLE 10

Sodium 4-(4-chlorophenyl)-2-(4,6-dimethylpyrimidin-2-ylthio)-nicotinate (Compound No. 307)

0.50 g (0.0012 mol) of 4-(4-chlorophenyl)-2-(4,6-dimethoxylpyrimidin-2-ylthio)nicotinic acid and 7 ml of ethanol were weighed, and 0.30 g (0.0016 mol) of methanol solution of 28% sodium methylate was dropwise added thereto at room temperature. After the dropwise addition, the mixture was further stirred at room temperature for 20 minutes. The crystal thus precipitated was filtrated, and was washed with ethanol and was dried to obtain 0.46 g of a white powder of the aimed product.

Yield: 86.0%, Melting point: 244°–247° C.

PREPARATION EXAMPLE 11

Synthesis of 2-(4,6-dimethoxylpyrimidin-2-ylthio)nicotinic acid (Compound No. 52)

4.0 g (0.026 mol) of 2-mercaptonicotinic acid, 5.7 g (0.026 mol) of 4,6-dimethoxyl-2-methylsulfonylpyrimidine and 7.2 g (0.052 mol) of potassium carbonate were weighed, and 70 ml of dimethylformamide was added thereto and the mixture was stirred at 80° C. for 2 hours. The resultant mixture was poured into water, and was washed with 100 ml of ethyl acetate. The aqueous layer was then acidified with 10% HCl aqueous solution to precipitate a crystal. The crystal thus precipitated was filtrated out, and was washed with water and was dried. The crystal was then recrystallized with methanol to obtain 5.3 g of a light-yellowish crystal of the aimed product.

Yield: 70.1%, Melting point: 165°–168° C.

PREPARATION EXAMPLE 12

Synthesis of ethoxymethyl 2-(4,6-dimethoxypyimidin-2-yloxy)-4-phenylnicotinate (Compound No. 86)

0.50 g (0.0014 mol) of 2-(4,6-dimethoxypyrimidin-2-yloxy)-4-phenylnicotinic acid and 0.24 g (0.0017 mol) of potassium carbonate were weighed, and 10 ml of dimethylformamide was added thereto and the mixture was stirred at room temperature for 1 hour. Thereafter, 0.14 g (0.0015 mol) of ethoxymethyl chloride was further added to the mixture, and the mixture was stirred at room temperature for 30 minutes. The mixture was then poured into water, and was extracted with 50 ml of ethyl acetate. The extracted material was washed with water and a saturated sodium chloride aqueous solution, and was dried with anhydrous sodium sulfate. After filtration, the solvent was distilled off, and the residue was purified by silica gel column chromatography (developing solvent: ethyl acetate/hexane =½) to obtain 0.54 g of a light-yellowish thick syrup-like aimed product.

Yield: 93.1%, Refractive-index ($n_{D20}$): 1.5701

PREPARATION EXAMPLE 13

Synthesis of 4-(3-chlorophenyl)-2-(4,6-dimethoxypyrimidin-2-ylthio)-N-methylsulfonynicotinamide (Compound No. 301)

3.0 g (0.0074 mol) of 4-(3-chlorophenyl)-2-(4,6-dimethoxypyrimidin-2-ylthio)nicotinic acid was weighed, and 30 ml of dimethylformamide was added thereto. Thereafter, 1.50 g (0.0093 mol) of carbonyldiimidazole was gradually added to the mixture under stirring, and the mixture was stirred at room temperature for 24 hours. 1.80 g (0.0019 mol) of methanesulfonamide and 0.60 g (0.0015 mol) of 60% sodium hydride were weighed, and 30 ml of dimethylformamide was added thereto and the mixture was stirred at 80° C. for 2 hours. Thereafter, the above prepared dimethylformamide solution of carbonylimidazole of nicotinic acid was added thereto at room temperature, and the mixture was stirred at 80° C. for 2 hours. The reaction mixture was then poured into water, and was washed with 50 ml of ethyl acetate. Thereafter, the aqueous layer was acidified with 10% HCl aqueous solution, and was extracted with 100 ml of ethyl acetate. The extracted material was washed with water and a saturated sodium chloride aqueous solution, and was dried with anhydrous sodium sulfate. After filtration, the solvent was distilled off, and the residue was purified by silica gel chromatography (developing solvent: ethyl acetate/hexane =1/1) to obtain 3.0 g of a light-yellowish glass-like aimed product.

Yield: 81.3%, Melting point: 54°–58° C.

PREPARATION EXAMPLE 14

Synthesis of benzyl 2-(4,6-dimethoxypyrimidin-2-ylamino)nicotinate (Compound No. 398)

2.3 g (0.01 mol) of benzyl 2-aminonicotinate, 2.2 g (0.01 mol) of 4,6-dimethoxy-2-methylsulfonylpyrimidine and 0.4 g (0.01 mol) of 60% sodium hydride were weighed, and 10 ml of dimethylformamide was added thereto and the mixture was stirred at 100° C. for 2 hours. The mixture was then poured into water, and was extracted with 100 ml of ethyl acetate. The extracted material was then washed with water and a saturated sodium chloride aqueous solution, and was dried with anhydrous sodium sulfate. After filtration, the solvent was distilled off, and the residue was recrystallized with ethanol to obtain 1.6 g of a yellow-brownish powder of the aimed product.

Yield: 43.0%, Melting point: 128°–131° C.

In the following, Preparation Examples of the intermediate products of the compound of the present invention are illustrated as Reference Examples. REFERENCE EXAMPLE 1

Synthesis of 1-cyano-1-methoxycarbonyl-4-(N,N-dimethylamino)-2-(4-methoxyphenyl)-1,3-butadiene 85.0 g (0.44 mol) of 1-cyano-1-methoxycarbonyl-2-(4-methoxyphenyl)-1-propylene and 1,1-dimethoxytrimethylamine (0.66 mol) were weighed, and 200 ml of methanol was added thereto and the mixture was refluxed for 30 minutes under stirring. The reaction mixture was cooled with ice water to precipitate a crystal, which was then filtrated out. The crystal thus obtained was washed three times with 100 ml of methanol, and was dried to obtain 103.6 g of a greenish yellow aimed product.

Yield: 81.4%, Melting point: 175°–178° C.

REFERENCE EXAMPLE 2

Synthesis of methyl-2-hydroxy-4-(4-methylphenyl)nicotinate 117.0 g (0.54 mol) of 1-cyano-1-methoxycarbonyl-4-(N,N-dimethylamino)-2-(4-methylphenyl)-1,3-butadiene was added to 250 ml of concentrated sulfuric acid at a temperature below 20° C. under stirring, and the mixture was stirred at room temperature for 48 hours. The reaction mixture was poured into 1 l of ice water, and the precipitated material was filtered out. The filtrate was adjusted to pH 6 with sodium hydroxide aqueous solution to precipitate the aimed product, which was then filtrated out. The material thus precipitated was washed with water and methanol, and was dried to obtain 74.9 g of a white crystal of the aimed product.

Yield: 60.9%, Melting point: 222°–224° C.

REFERENCE EXAMPLE 3

Synthesis of methyl-2-bromo-4-(4chlorophenyl)nicotinate 80.0 g (0.28 mol) of 1-cyano-1-methoxycarbonyl-4-(N,N-dimethylamino)-2-(4-chlorophenyl)-1,3-butadiene was weighed, and 100 ml of acetic acid was added thereto and an acetic acid solution of 25% HBr was then gradually added dropwise thereto at room temperature under stirring. After the dropwise addition, the resultant mixture was stirred at room temperature for 3 hours. The reaction mixture was then poured into ice water to precipitate a crystal. The crystal thus precipitated was filtrated out and washed with water and was dried to obtain 75.0 g of a white crystal of the aimed product.

Yield: 83.5%, Melting point: 73°–76° C.

REFERENCE EXAMPLE 4

Synthesis of 2-bromo-4-(4-chlorophenyl)nicotinic acid 50.0 g (0.15 mol) of methyl 2-bromo-4-(4-chlorophenyl)nicotinate was weighed, and 300 ml of dimethylsulfoxide and 60 ml of 30% sodium hydroxide aqueous solution were added thereto and the mixture was stirred at 80° C. for 3 hours. The mixture was then poured into water and was washed with 300 ml of ethyl acetate. Thereafter, the aqueous layer was acidified with 10% HCl aqueous solution to precipitate a crystal, which was then filtrated out. The crystal thus precipitated was washed with water and isopropyl ether, and was dried to obtain 41.0 g of a white crystal of the aimed product.

Yield: 85.7%, Melting point: 204°–208° C.

In the following, examples of the compound of the present invention thus obtained are illustrated in Table 1. The abbreviation marks in the Table respectively mean the following groups.

Compound Nos. given in the Table will be referred to the subsequent description in the specification.

Pym: 4,6-Dimethoxypyrimidin-2-yl group
Tri: 4,6-Dimethoxytriazin-2-yl group
Ph: Phenyl group
(a): 2-(4,6-Dimethylpyrimidin-2-yl)oxy group
(b): 2-(4-Difluoromethoxy-6-methoxypyrimidin-2-yl)oxy group
(c): 2-(4-Chloro-6-methoxypyrimidin-2-yl)oxy group
(d): 2-(4-Methoxy-6-methylpyrimidin-2-yl)oxy group
(e): 2-(4-Dimethylamino-6-methoxypyrimidin-2-yl)oxy group
(f): 2-(4-Methoxypyrimidin-2-yl)oxy group
(g): 2-(4,6-Dimethylpyrimidin-2-yl)thio group
(h): 2-(4-Methoxy-6-methyltriazin-2-yl)thio group
(i): 2-(4-methoxy-6-methylpyrimidin-2-yl)thio group
(j): 2-(4,6-Dimethoxypyrimidin-2-yl)amino group
(k): 2-[N-formyl-(4,6-dimethoxypyrimidin-2-yl)amino] group
(l): 2-[(N-methoxycarbonyl-(4,6-dimethoxypyrimidin-2-yl) amino] group
(m): 2-(4-Chloro-6-methoxypyrimidin-2-yl)thio group Also, examples of the intermediate products as prepared above, are given in the following Table 2, Table 3 and Table 4.

TABLE 1

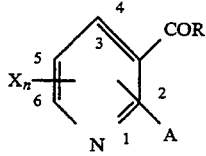

| Compound No. | R | Xn | A | Physical properties Melting point (°C.) or Refractive index ($n_D^{20}$) |
| --- | --- | --- | --- | --- |
| 1 | OH | 4,6-(CH$_3$)$_2$ | 2-O-Pym | 194~196 |
| 2 | OK | 4,6-(CH$_3$)$_2$ | 2-O-Pym | 188~195 |
| 3 | OH | H | 2-O-Pym | 134~141 |
| 4 | OH | 2-Ph, 6-CH$_3$ | 4-O-Pym | 277~284 |
| 5 | OH | 2-Ph | 4-O-Pym | 166~174 |
| 6 | OH | 6-CH$_3$ | 2-O-Pym | 174~177 |
| 7 | OH | 4-Ph | 2-O-Pym | 165~169 |
| 8 | OH | 2,6-(CH$_3$)$_2$ | 4-O-Pym | 191~199 |
| 9 | OCH$_3$ | H | 2-O-Pym | 1.6425 |
| 10 | OC$_2$H$_5$ | 2,6-(CH$_3$)$_2$ | 4-O-Pym | 1.5289 |
| 11 | OCH$_3$ | 6-CH$_3$ | 2-O-Pym | 99~103 |
| 12 | OCH$_3$ | 2-OCH$_3$ | 4-O-Pym | 100~101.5 |

TABLE 1-continued
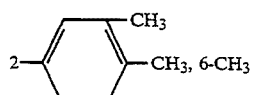
| Compound No. | R | Xn | A | Physical properties Melting point (°C.) or Refractive index ($n_D^{20}$) |
|---|---|---|---|---|
| 13 | OCH$_3$ | 2-Ph, 4-CH$_3$ | 6-O-Pym | 1.5609 |
| 14 | OCH$_3$ | 2-Ph, 6-CH$_3$ | 4-O-Pym | 96~99 |
| 15 | OCH$_3$ | 2-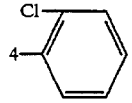-CH$_3$, 6-CH$_3$ | 4-O-Pym | 113~114 |
| 16 | OC$_2$H$_5$ | 4,6-(CH$_3$)$_2$ | 2-O-Pym | 74~75 |
| 17 | OCH$_2$-Ph | 2-Ph, 6-CH$_3$ | 4-O-Pym | 1.5723 |
| 18 | OCH$_3$ | 4-Ph | 2-O-Pym | 111~115 |
| 19 | OCH$_3$ | 4-OCH$_3$ | 2-O-Pym | 117~119 |
| 20 | OH | 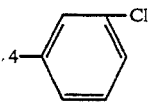 | 2-O-Pym | 176.5~182 |
| 21 | OH | 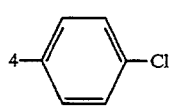 | 2-O-Pym | 137.5~140 |
| 22 | OH | 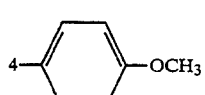 | 2-O-Pym | 186~192 |
| 23 | OH | 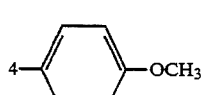 | 2-O-Pym | 186~189 |
| 24 | OCH$_3$ | 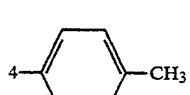 | 2-O-Pym | 136~139.5 |
| 25 | OH | 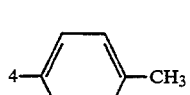 | 2-O-Pym | 170~174 |
| 26 | OCH$_3$ | 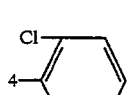 | 2-O-Pym | 152~153.5 |
| 27 | OCH$_3$ | 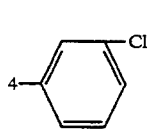 | 2-O-Pym | 103~106 |
| 28 | OCH$_3$ | 4-⌬-Cl | 2-O-Pym | unmeasurable |

TABLE 1-continued

[Structure: pyridine ring with positions labeled, COR at position 3, A at position 2, X_n on ring, N at position 1]

| Compound No. | R | Xn | A | Physical properties Melting point (°C.) or Refractive index ($n_D^{20}$) |
|---|---|---|---|---|
| 29 | OCH$_3$ | 4-(4-Cl-C$_6$H$_4$) | 2-O-Pym | 149~155 |
| 30 | OH | 4-CH$_3$ | 2-O-Pym | 181.5~183.5 |
| 31 | OCH$_3$ | 4-CH$_3$ | 2-O-Pym | |
| 32 | OH | 4-OCH$_3$ | 2-O-Pym | |
| 33 | OH | 4-Cl | 2-O-Pym | 168~172 |
| 34 | OCH$_3$ | 4-Cl | 2-O-Pym | |
| 35 | OH | 4-CF$_3$, 6-CH$_3$ | 2-O-Pym | 166~171 |
| 36 | OCH$_3$ | 4-CF$_3$, 6-CH$_3$ | 2-O-Pym | |
| 37 | OH | 4,6-(Ph)$_2$ | 2-O-Pym | |
| 38 | OCH$_3$ | 4,6-(Ph)$_2$ | 2-O-Pym | |
| 39 | OH | 4-Ph, 5-CH$_3$ | 2-O-Pym | |
| 40 | OCH$_3$ | 4-Ph, 5-CH$_3$ | 2-O-Pym | |
| 41 | OH | 4,5,6-(CH$_3$)$_3$ | 2-O-Pym | 205.5~209 |
| 42 | O(CH$_2$)$_2$—Si(CH$_3$)$_3$ | 4,5,6-(CH$_3$)$_3$ | 2-O-Pym | 78~81 |
| 43 | OH | 4-N(CH$_3$)$_2$ | 2-O-Pym | |
| 44 | OCH$_3$ | 4-N(CH$_3$)$_2$ | 2-O-Pym | |
| 45 | OH | 4-NH(CH$_3$) | 2-O-Pym | |
| 46 | OCH$_3$ | 4-NH(CH$_3$) | 2-O-Pym | |
| 47 | OH | 4-Ph, 6-CH$_3$ | 2-O-Pym | 188~191 |
| 48 | OCH$_3$ | 4-Ph, 6-CH$_3$ | 2-O-Pym | 137~139 |
| 49 | OH | 4-(C$_6$H$_4$)-CH$_3$, 6-CH$_3$ | 2-O-Pym | 166~171 |
| 50 | OCH$_3$ | 4-(C$_6$H$_4$)-CH$_3$, 6-CH$_3$ | 2-O-Pym | 168~170 |
| 51 | OH | 4-Ph | 2-S-Pym | 191~195 |
| 52 | OH | H | 2-S-Pym | 165~168 |
| 53 | OCH$_3$ | 4-Ph | 2-S-Pym | 115~117 |
| 54 | OCH$_3$ | H | 2-S-Pym | 107~110 |
| 55 | OH | 4-Ph | 2-NH-Pym | |
| 56 | OCH$_3$ | 4-Ph | 2-NH-Pym | |
| 57 | OH | 4-Cl | 2-S-Pym | |
| 58 | OCH$_3$ | H | 2-S-Tri | 78~79 |
| 59 | OCH$_3$ | 4-Cl | 2-S-Pym | |

TABLE 1-continued

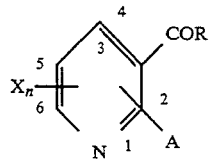

| Compound No. | R | Xn | A | Physical properties Melting point (°C.) or Refractive index ($n_D^{20}$) |
|---|---|---|---|---|
| 60 | OH | 4-Ph | (a) | |
| 61 | OCH₃ | 4-Ph | (a) | |
| 62 | OH | 4-Ph | (b) | |
| 63 | OH | 4-Ph | (c) | |
| 64 | OH | 4-Ph | (d) | |
| 65 | OH | 4-Ph | (e) | |
| 66 | OH | H | 2-O-Tri | |
| 67 | OCH₃ | H | 2-O-Tri | |
| 68 | OH | 4-Ph | 2-O-Tri | |
| 69 | OCH₃ | 4-Ph | 2-O-Tri | |
| 70 | H | 4-Ph | 2-O-Pym | |
| 71 | OCH₃ | 2-Ph | 4-O-Pym | |
| 72 | OH | 2-CH₃ | 4-O-Pym | |
| 73 | OC₂H₅ | 2-CH₃ | 4-O-Pym | 86~87 |
| 74 | OH | 2-Br | 4-O-Pym | |
| 75 | OH | 2-Br | 4-S-Pym | |
| 76 | OCH₃ | 4-C₃H₇-i | 2-O-Pym | 78~83 |
| 77 | OH | 4-C₃H₇-i | 2-O-Pym | 169~173 |
| 78 | OCH₂-Ph | 4-C₃H₇-i, 6-CH₃ | 2-O-Pym | 84~87 |
| 79 | OH | 4-C₃H₇-i, 6-CH₃ | 2-O-Pym | 185~188 |
| 80 | OCH₃ | 4-(phenyl-CH₃) | 2-O-Pym | |
| 81 | OH | 4-(phenyl-CH₃) | 2-O-Pym | 157.5~159 |
| 82 | OCH₃ | 4-(phenyl-(CH₃)₂) | 2-O-Pym | |
| 83 | OH | 4-(phenyl-(CH₃)₂) | 2-O-Pym | |
| 84 | OH | 4-C₃H₇-i | 2-S-Pym | 169~173.5 |
| 85 | OH | 4-Ph | (f) | |
| 86 | OCH₂OC₂H₅ | 4-Ph | 2-O-Pym | 1.5701 |
| 87 | OCH₂OCOC₄H₉-t | 4-Ph | 2-O-Pym | 1.5440 |
| 88 | OCH₂OCOC₄H₉-t | 4-Ph | 2-S-Pym | 1.5712 |
| 89 | OCHOCOC₄H₉-n (CH₃) | 4-Ph | 2-S-Pym | 1.5670 |
| 90 | OH | 4-Ph, 6-CH₃ | 2-S-Pym | 154~159 |
| 91 | OH | 4-(phenyl-CH₃) | 2-S-Pym | 179~183.5 |
| 92 | OCH₃ | 4-(phenyl-CH₃) | 2-S-Pym | 149~151 |

TABLE 1-continued

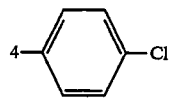

| Compound No. | R | Xn | A | Physical properties Melting point (°C.) or Refractive index ($n_D^{20}$) |
|---|---|---|---|---|
| 93 | OCH$_3$ | 4-(C$_6$H$_4$)-Cl | 2-S-Pym | 138~141.5 |
| 94 | OH | 4-(C$_6$H$_4$)-Cl | 2-S-Pym | 219~223 |
| 95 | OCH$_3$ | 5-Cl | 2-S-Pym | 74~76 |
| 96 | OH | 5-Cl | 2-S-Pym | 150~154 |
| 97 | OCH$_3$ | 4-(C$_6$H$_4$)-Cl (2-Cl) | 2-S-Pym | 1.6042 |
| 98 | OH | 4-(C$_6$H$_4$)-Cl (2-Cl) | 2-S-Pym | 181~184 |
| 99 | OCH$_3$ | 4-(C$_6$H$_4$)(CH$_3$)$_2$ | 2-S-Pym | 1.5961 |
| 100 | OH | 4-(C$_6$H$_4$)(CH$_3$)$_2$ | 2-S-Pym | 95~99 |
| 101 | OCH$_3$ | 4-(C$_6$H$_4$)-F | 2-S-Pym | 151~154 |
| 102 | OH | 4-(C$_6$H$_4$)-F | 2-S-Pym | 193~197 |
| 103 | OCH$_3$ | 4-(C$_6$H$_4$)-F, 6-CH$_3$ | 2-S-Pym | 120~123 |
| 104 | OH | 4-(C$_6$H$_4$)-F, 6-CH$_3$ | 2-S-Pym | 155.5~158 |
| 105 | OCH$_2$OCOC$_4$H$_9$-t | 4-(C$_6$H$_4$)(CH$_3$)$_2$ | 2-S-Pym | 1.5640 |

TABLE 1-continued
| Compound No. | R | Xn | A | Physical properties Melting point (°C.) or Refractive index ($n_D^{20}$) |
|---|---|---|---|---|
| 106 | OCH$_2$OCOC$_4$H$_9$-t | 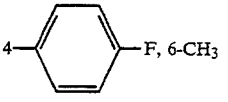 4-F | 2-S-Pym | 1.5615 |
| 107 | OCH$_2$OCOC$_4$H$_9$-t | 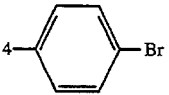 4-F, 6-CH$_3$ | 2-S-Pym | 1.5619 |
| 108 | OCH$_3$ |  4-Br | 2-S-Pym | 134~137.5 |
| 109 | OH | 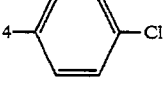 4-Br | 2-S-Pym | 178~181 |
| 110 | OCH$_3$ | 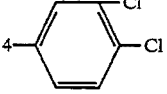 4-Cl, Cl | 2-S-Pym | 135~139 |
| 111 | OH | 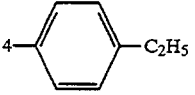 4-Cl, Cl | 2-S-Pym | 169~172 |
| 112 | OCH$_3$ | 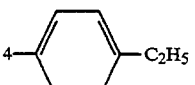 4-C$_2$H$_5$ | 2-S-Pym | 90.5~94 |
| 113 | OH | 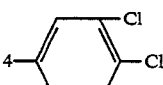 4-C$_2$H$_5$ | 2-S-Pym | 178~180 |
| 114 | OCH$_2$OCOC$_4$H$_9$-t | 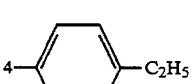 4-Cl, Cl | 2-S-Pym | 1.5796 |
| 115 | OCH$_2$OCOC$_4$H$_9$-t | 4-C$_2$H$_5$ | 2-S-Pym | 1.5687 |
| 116 | OCH$_3$ | 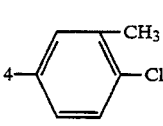 4-CH$_3$, Cl | 2-S-Pym | 74~78 |

TABLE 1-continued $$X_n \underset{6}{\overset{5}{\underset{N}{\bigcirc}}}\underset{1}{\overset{3}{\underset{2}{\bigvee}}}\overset{4}{\underset{A}{\overset{COR}{}}}$$

| Compound No. | R | Xn | A | Physical properties Melting point (°C.) or Refractive index ($n_D^{20}$) |
|---|---|---|---|---|
| 117 | OH | 4-(2-CH₃, 4-Cl-phenyl) | 2-S-Pym | 170.5~174 |
| 118 | OCH₃ | 4-(4-NO₂-phenyl) | 2-S-Pym | unmeasurable |
| 119 | OH | 4-(4-NO₂-phenyl) | 2-S-Pym | 160~162 |
| 120 | OCH₃ | 4-(4-CF₃-phenyl) | 2-S-Pym | 1.5681 |
| 121 | OH | 4-(4-CF₃-phenyl) | 2-S-Pym | 179~182 |
| 122 | OCH₃ | 4-(4-C₃H₇-i-phenyl) | 2-S-Pym | 1.5786 |
| 123 | OH | 4-(4-C₃H₇-i-phenyl) | 2-S-Pym | 173~176 |
| 124 | OCH₃ | 4-Ph, 5-CH₃ | 2-S-Pym | 150~153 |
| 125 | OH | 4-Ph, 5-CH₃ | 2-S-Pym | 140~143 |
| 126 | OCH₂OCOC₄H₉-t | 4-(4-CF₃-phenyl) | 2-S-Pym | 1.5409 |
| 127 | OCH₂OCOC₄H₉-t | 4-(4-C₃H₇-i-phenyl) | 2-S-Pym | 1.5641 |
| 128 | OCH₃ | 4-(4-F-phenyl) | 2-S-Pym | 117~120 |
| 129 | OH | 4-(4-F-phenyl) | 2-S-Pym | 199.5~202 |

TABLE 1-continued

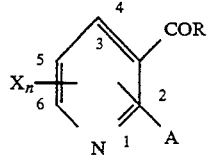

| Compound No. | R | Xn | A | Physical properties Melting point (°C.) or Refractive index ($n_D^{20}$) |
|---|---|---|---|---|
| 130 | OCH$_3$ | 4-(C$_6$H$_4$)-OCH$_3$ | 2-S-Pym | 107~110 |
| 131 | OH | 4-(C$_6$H$_4$)-OCH$_3$ | 2-S-Pym | 198~201 |
| 132 | OCH$_2$OCOC$_4$H$_9$-t | 4-(C$_6$H$_4$)-F | 2-S-Pym | 1.5659 |
| 133 | OCH$_3$ | 4-(C$_6$H$_4$)-CH$_3$ | 2-S-Pym | 1.5990 |
| 134 | OH | 4-(C$_6$H$_4$)-CH$_3$ | 2-S-Pym | 182~184 |
| 135 | OCH$_2$OCOC$_4$H$_9$-t | 4-(C$_6$H$_4$)-CH$_3$ | 2-S-Pym | 1.5625 |
| 136 | OCH$_3$ | 4-(C$_6$H$_3$)-3,4-F$_2$ | 2-S-Pym | 118~121 |
| 137 | OH | 4-(C$_6$H$_3$)-3,4-F$_2$ | 2-S-Pym | 185~187 |
| 138 | OCH$_3$ | 4-(C$_6$H$_4$)-Cl | 2-S-Pym | 1.6074 |
| 139 | OH | 4-(C$_6$H$_4$)-Cl | 2-S-Pym | 187~190 |
| 140 | OCH$_3$ | 4-Ph, 5-C$_2$H$_5$ | 2-S-Pym | 143.5~146 |
| 141 | OH | 4-Ph, 5-C$_2$H$_5$ | 2-S-Pym | 163~166.5 |
| 142 | OH | 4-Ph, 5-CH$_3$ | 2-S-Pym | 157~162 |

TABLE 1-continued

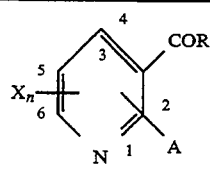

| Compound No. | R | Xn | A | Physical properties Melting point (°C.) or Refractive index ($n_D^{20}$) |
|---|---|---|---|---|
| 143 | OH | 4-(C₃H₇-phenyl) | 2-S-Pym | 156.5~160 |
| 144 | OCH₂OCOC₄H₉-t | 4-(C₃H₇-phenyl) | 2-S-Pym | 1.5719 |
| 145 | OCH₂OCOC₄H₉-t | 4-(Cl-phenyl) | 2-S-Pym | 1.5719 |
| 146 | OH | 4-(piperidinyl-phenyl) | 2-S-Pym | 188~192 |
| 147 | OH | 4-(F-phenyl) | 2-O-Pym | 178~181 |
| 148 | OCH₂OCOC₄H₉-t | 4-(F-phenyl) | 2-O-Pym | 1.5456 |
| 149 | OCH₃ | 4-(C₂H₅-phenyl) | 2-O-Pym | 112~115 |
| 150 | OH | 4-(C₂H₅-phenyl) | 2-O-Pym | 190~192 |
| 151 | OCH₃ | 5-Br | 2-O-Tri | |
| 152 | OH | 4-Br, 6-CH₃ (phenyl) | 2-O-Pym | 216.5~218 |
| 153 | OCH₃ | 4-C₂H₅, 6-CH₃ (phenyl) | 2-O-Pym | 117~121 |
| 154 | OH | 4-C₂H₅, 6-CH₃ (phenyl) | 2-O-Pym | 191~193.5 |

TABLE 1-continued

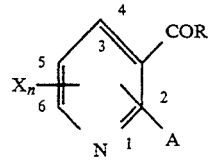

| Compound No. | R | Xn | A | Physical properties Melting point (°C.) or Refractive index ($n_D^{20}$) |
|---|---|---|---|---|
| 155 | OCH$_3$ | 4-C$_6$H$_4$-OC$_2$H$_5$ | 2-S-Pym | 96~100 |
| 156 | OH | 4-C$_6$H$_4$-OC$_2$H$_5$ | 2-S-Pym | 178~181 |
| 157 | OCH$_3$ | 4-C$_6$H$_4$-OC$_3$H$_7$ | 2-S-Pym | 1.5976 |
| 158 | OH | 4-C$_6$H$_4$-OC$_3$H$_7$ | 2-S-Pym | 172.5~174.5 |
| 159 | OH | 4-C$_6$H$_4$-Br | 2-O-Pym | 189~193 |
| 160 | OC$_2$H$_5$ | 4-C$_6$H$_4$-Br | 2-O-Pym | 106.5~108 |
| 161 | OCH$_2$OCOC$_4$H$_9$-t | 4-C$_6$H$_4$-Br | 2-O-Pym | 1.5576 |
| 162 | OCH$_3$ | 4-C$_6$H$_3$(OCH$_3$)$_2$ | 2-S-Pym | 146~148 |
| 163 | OH | 4-C$_6$H$_3$(OCH$_3$)$_2$ | 2-S-Pym | 184.5~187 |
| 164 | OCH$_3$ | 4-C$_6$H$_3$(OCH$_3$)$_2$ | 2-O-Pym | 169.5~171 |
| 165 | OH | 4-C$_6$H$_3$(OCH$_3$)$_2$ | 2-O-Pym | 165~169 |

TABLE 1-continued

[Structure: pyridine ring with positions labeled N-1, 2-A, 3, 4, 5, 6; X_n substituent on ring; position 2 bears a group with COR at position 4]

| Compound No. | R | Xn | A | Physical properties Melting point (°C.) or Refractive index ($n_D^{20}$) |
|---|---|---|---|---|
| 166 | OCH$_3$ | 4-Br-phenyl | 2-S-Pym | 1.6091 |
| 167 | OH | 4-Br-phenyl | 2-S-Pym | 174~176 |
| 168 | OH | 4-F-phenyl | 2-O-Pym | 177~179 |
| 169 | OCH$_3$ | 4-C$_3$H$_7$-phenyl | 2-O-Pym | 86~88 |
| 170 | OH | 4-C$_3$H$_7$-phenyl | 2-O-Pym | 183~185 |
| 171 | OH | 4-Br-phenyl | 2-O-Pym | 161~163.5 |
| 172 | OCH$_3$ | 4-CH$_3$-phenyl | 2-S-Pym | 125~127 |
| 173 | OH | 4-CH$_3$-phenyl | 2-S-Pym | 201~203.5 |
| 174 | OCH$_3$ | 4-CH$_3$-phenyl | 2-O-Pym | 131~134 |
| 175 | OH | 4-CH$_3$-phenyl | 2-O-Pym | 162~165 |
| 176 | OCH$_3$ | 4-F-phenyl | 2-S-Pym | 1.5907 |

TABLE 1-continued

| Compound No. | R | Xn | A | Physical properties Melting point (°C.) or Refractive index ($n_D^{20}$) |
|---|---|---|---|---|
| 177 | OH | 4-F-C₆H₄ | 2-S-Pym | 170~172 |
| 178 | OCH₃ | 4-(i-C₃H₇O)-C₆H₄ | 2-S-Pym | 1.5831 |
| 179 | OH | 4-(i-C₃H₇O)-C₆H₄ | 2-S-Pym | 177~179 |
| 180 | OCH₃ | 4-(i-C₃H₇O)-C₆H₄ | (g) | 1.5965 |
| 181 | OH | 4-(i-C₃H₇O)-C₆H₄ | (g) | 172~174 |
| 182 | OCH₃ | 4-Ph | (h) | |
| 183 | OH | 4-Ph | (h) | 125~128 |
| 184 | OCH₃ | 4-Ph | (g) | |
| 185 | OH | 4-Ph | (g) | 145~150 |
| 186 | OCH₂OCOC₄H₉ | 4-Ph | 2-S-Tri | 1.5562 |
| 187 | OCH₂OCOC₄H₉-t | 4-Ph | 2-S-Tri | unmeasurable |
| 188 | OCH₂OCOC₄H₉-t | 4-Cl | 2-O-Pym | |
| 189 | OCH₂OCOC₄H₉-t | 4-Cl | 2-S-Pym | |
| 190 | OCH₃ | 4-Br | 2-O-Pym | |
| 191 | OH | 4-Br | 2-O-Pym | |
| 192 | OCH₂OCOC₄H₉-t | 4-Br | 2-O-Pym | |
| 193 | OCH₃ | 4-Br | 2-S-Pym | |
| 194 | OH | 4-Br | 2-S-Pym | |
| 195 | OCH₂OCOC₄H₉-t | 4-Br | 2-S-Pym | |
| 196 | OCH₃ | 4-O-Ph | 2-O-Pym | |
| 197 | OH | 4-O-Ph | 2-O-Pym | |
| 198 | OCH₂OCOC₄H₉-t | 4-O-Ph | 2-O-Pym | |
| 199 | OCH₃ | 4-O-Ph | 2-S-Pym | |
| 200 | OH | 4-O-Ph | 2-S-Pym | |
| 201 | OCH₂OCOC₄H₉-t | 4-O-Ph | 2-S-Pym | |
| 202 | OCH₃ | 4-S-Ph | 2-O-Pym | |
| 203 | OH | 4-S-Ph | 2-O-Pym | |
| 204 | OCH₂OCOC₄H₉-t | 4-S-Ph | 2-O-Pym | |
| 205 | OCH₃ | 4-S-Ph | 2-S-Pym | |
| 206 | OH | 4-S-Ph | 2-S-Pym | |
| 207 | OCH₂OCOC₄H₉-t | 4-S-Ph | 2-S-Pym | |
| 208 | OCH₃ | 4-S-(2-Cl-C₆H₄) | 2-S-Pym | |
| 209 | OH | 4-S-(2-Cl-C₆H₄) | 2-S-Pym | |

TABLE 1-continued

| Compound No. | R | Xn | A | Physical properties Melting point (°C.) or Refractive index ($n_D^{20}$) |
|---|---|---|---|---|
| 210 | OCH$_2$OCOC$_4$H$_9$-t | 4-S-(phenyl)-Cl | 2-S-Pym | |
| 211 | OCH$_3$ | 4-S-(phenyl)-Cl | 2-S-Pym | |
| 212 | OH | 4-S-(phenyl)-Cl | 2-S-Pym | |
| 213 | OCH$_2$OCOC$_4$H$_9$-t | 4-S-(phenyl)-Cl | 2-S-Pym | |
| 214 | OCH$_3$ | 4-S-(phenyl)-Cl | 2-S-Pym | |
| 215 | OH | 4-S-(phenyl)-Cl | 2-S-Pym | |
| 216 | OCH$_2$OCOC$_4$H$_9$-t | 4-S-(phenyl)-Cl | 2-S-Pym | |
| 217 | OCH$_3$ | 4-O-(phenyl)-Cl | 2-S-Pym | |
| 218 | OH | 4-O-(phenyl)-Cl | 2-S-Pym | |
| 219 | OCH$_2$OCOC$_4$H$_9$-t | 4-O-(phenyl)-Cl | 2-S-Pym | |
| 220 | OCH$_3$ | 4-O-(phenyl)-Cl | 2-S-Pym | |

TABLE 1-continued

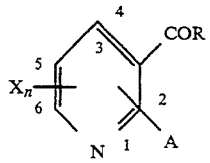

| Compound No. | R | Xn | A | Physical properties Melting point (°C.) or Refractive index ($n_D^{20}$) |
|---|---|---|---|---|
| 221 | OH | 4-O—C₆H₄—Cl (3-Cl) | 2-S-Pym | |
| 222 | OCH₂OCOC₄H₉-t | 4-O—C₆H₄—Cl (3-Cl) | 2-S-Pym | |
| 223 | OCH₃ | 4-O—C₆H₄—Cl (4-Cl) | 2-S-Pym | |
| 224 | OH | 4-O—C₆H₄—Cl (4-Cl) | 2-S-Pym | |
| 225 | OCH₂OCOC₄H₉-t | 4-O—C₆H₄—Cl (4-Cl) | 2-S-Pym | |
| 226 | OCH₃ | 4-S—C₆H₄—CH₃ (3-CH₃) | 2-S-Pym | |
| 227 | OH | 4-S—C₆H₄—CH₃ (3-CH₃) | 2-S-Pym | |
| 228 | OCH₂OCOC₄H₉-t | 4-S—C₆H₄—CH₃ (3-CH₃) | 2-S-Pym | |
| 229 | OCH₃ | 4-S—C₆H₄—CH₃ (4-CH₃) | 2-S-Pym | |
| 230 | OH | 4-S—C₆H₄—CH₃ (4-CH₃) | 2-S-Pym | |
| 231 | OCH₂OCOC₄H₉-t | 4-S—C₆H₄—CH₃ (4-CH₃) | 2-S-Pym | |

TABLE 1-continued

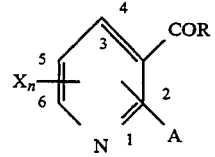

| Compound No. | R | Xn | A | Physical properties Melting point (°C.) or Refractive index ($n_D^{20}$) |
|---|---|---|---|---|
| 232 | OCH$_3$ | 4-S—C$_6$H$_4$—CH$_3$ | 2-S-Pym | |
| 233 | OH | 4-S—C$_6$H$_4$—CH$_3$ | 2-S-Pym | |
| 234 | OCH$_2$OCOC$_4$H$_9$-t | 4-S—C$_6$H$_4$—CH$_3$ | 2-S-Pym | |
| 235 | OCH$_3$ | 2-CH$_3$O, 4-S—C$_6$H$_3$ | 2-S-Pym | |
| 236 | OH | 2-CH$_3$O, 4-S—C$_6$H$_3$ | 2-S-Pym | |
| 237 | OCH$_2$OCOC$_4$H$_9$-t | 2-CH$_3$O, 4-S—C$_6$H$_3$ | 2-S-Pym | |
| 238 | OCH$_3$ | 3-OCH$_3$, 4-S—C$_6$H$_3$ | 2-S-Pym | |
| 239 | OH | 3-OCH$_3$, 4-S—C$_6$H$_3$ | 2-S-Pym | |
| 240 | OCH$_2$OCOC$_4$H$_9$-t | 3-OCH$_3$, 4-S—C$_6$H$_3$ | 2-S-Pym | |
| 241 | OCH$_3$ | 4-S—C$_6$H$_4$—OCH$_3$ | 2-S-Pym | |
| 242 | OH | 4-S—C$_6$H$_4$—OCH$_3$ | 2-S-Pym | |

TABLE 1-continued

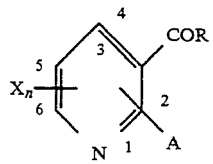

| Compound No. | R | Xn | A | Physical properties Melting point (°C.) or Refractive index ($n_D^{20}$) |
|---|---|---|---|---|
| 243 | OCH$_2$OCOC$_4$H$_9$-t | 4-S—C$_6$H$_4$—OCH$_3$ | 2-S-Pym | |
| 244 | OH | 4-O—C$_6$H$_4$(CH$_3$) (2-CH$_3$) | 2-O-Pym | |
| 245 | OH | 4-O—C$_6$H$_4$(CH$_3$) (3-CH$_3$) | 2-O-Pym | |
| 246 | OH | 4-O—C$_6$H$_4$—CH$_3$ | 2-O-Pym | |
| 247 | OH | 4-S—C$_6$H$_4$—OCH$_3$ (2-OCH$_3$) | 2-O-Pym | |
| 248 | OH | 4-O—C$_6$H$_4$—OCH$_3$ (3-OCH$_3$) | 2-O-Pym | |
| 249 | OH | 4-O—C$_6$H$_4$—OCH$_3$ | 2-O-Pym | |
| 250 | OH | 4-COCH$_3$ | 2-O-Pym | |
| 251 | OH | 4-C(CH$_3$)=NOCH$_3$ | 2-O-Pym | |
| 252 | OH | 4-COCH$_3$ | 2-S-Pym | |
| 253 | OH | 4-C(CH$_3$)=NOCH$_3$ | 2-S-Pym | |
| 254 | OH | 4-O—C$_6$H$_4$(CH$_3$) (2-CH$_3$) | 2-S-Pym | |
| 255 | OH | 4-O—C$_6$H$_4$(CH$_3$) (3-CH$_3$) | 2-S-Pym | |

TABLE 1-continued
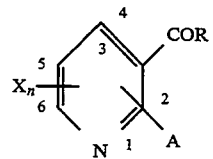
| Compound No. | R | Xn | A | Physical properties Melting point (°C.) or Refractive index ($n_D^{20}$) |
|---|---|---|---|---|
| 256 | OH | 4-O—C6H4—OCH3 (4-O, 4'-OCH3) | 2-S-Pym | |
| 257 | OH | 4-O—C6H4 (CH3O-, 4-O) | 2-S-Pym | |
| 258 | OH | 4-O—C6H4—OCH3 (3-OCH3) | 2-S-Pym | |
| 259 | OH | 4-O—C6H4—OCH3 | 2-S-Pym | |
| 260 | OH | 4-S—C6H4—Cl | 2-O-Pym | |
| 261 | OH | 4-S—C6H4—Cl | 2-O-Pym | |
| 262 | OH | 4-S—C6H4—Cl | 2-O-Pym | |
| 263 | OH | 4-S—C6H4 (CH3-) | 2-O-Pym | |
| 264 | OH | 4-S—C6H4—CH3 | 2-O-Pym | |
| 265 | OH | 4-S—C6H4—CH3 | 2-O-Pym | |
| 266 | OH | 4-S—C6H4 (CH3O-) | 2-O-Pym | |

TABLE 1-continued

[Structure: pyridine ring with COR at position 3, X$_n$ at positions 5/6, A at position 2, N at position 1]

| Compound No. | R | Xn | A | Physical properties Melting point (°C.) or Refractive index (n$_D^{20}$) |
|---|---|---|---|---|
| 267 | OH | 4-S-(phenyl with 3-OCH$_3$) | 2-O-Pym | |
| 268 | OH | 4-S-(phenyl with 4-OCH$_3$) | 2-O-Pym | |
| 269 | OH | 4-NH-Ph | 2-S-Pym | |
| 270 | OH | 4-CH$_3$-Ph | 2-S-Pym | |
| 271 | OH | 4-(phenyl with 2-Br, N(CH$_3$)$_2$) | 2-S-Pym | |
| 272 | OH | 4-(phenyl with 2-CH$_3$, N(CH$_3$)$_2$) | 2-S-Pym | |
| 273 | OH | 4-(phenyl with 2-Cl, N(CH$_3$)$_2$) | 2-S-Pym | |
| 274 | OH | 4-COC$_2$H$_5$ | 2-S-Pym | |
| 275 | OH | 4-C(C$_2$H$_5$)=N—OCH$_3$ | 2-S-Pym | |
| 276 | OH | 4-C(CH$_3$)=N—OC$_2$H$_5$ | 2-S-Pym | |
| 277 | OH | 4-CH=N—OCH$_3$ | 2-S-Pym | |
| 278 | OH | 4-CH$_2$-(4-Cl-phenyl) | 2-S-Pym | |
| 279 | OH | 4-COOH | 2-S-Pym | |
| 280 | OCH$_3$ | 4-COOCH$_3$ | 2-S-Pym | |
| 281 | OH | 4-COOCH$_3$ | 2-S-Pym | |
| 282 | SCH$_3$ | 4-Ph | 2-S-Pym | |
| 283 | H | 4-Ph | 2-S-Pym | |
| 284 | OH | 2-Ph | 4-S-Pym | |
| 285 | OH | 2-(4-Cl-phenyl) | 4-S-Pym | |
| 286 | OH | 4-(4-SCH$_3$-phenyl) | 2-S-Pym | |

TABLE 1-continued

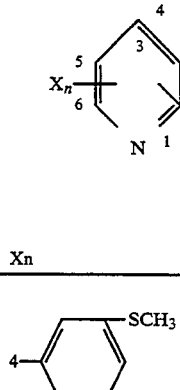

| Compound No. | R | Xn | A | Physical properties Melting point (°C.) or Refractive index ($n_D^{20}$) |
|---|---|---|---|---|
| 287 | OH | 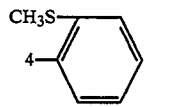 4-position, SCH₃ at another position | 2-S-Pym | |
| 288 | OH | CH₃S- phenyl, 4- | 2-S-Pym | |
| 289 | OH | 4-phenyl-SCH₃ | 2-O-Pym | |
| 290 | OH | phenyl with SCH₃, 4- | 2-O-Pym | |
| 291 | OH | CH₃S-phenyl, 4- | 2-O-Pym | |
| 292 | OH | 4-SCH₃ | 2-S-Pym | |
| 293 | OH | 4-NH-phenyl-Cl | 2-S-Pym | |
| 294 | OH | 4-NH-phenyl-Cl | 2-S-Pym | |
| 295 | OH | 4-NH-phenyl-Cl | 2-S-Pym | |
| 296 | OH | 4-SC₂H₅ | 2-S-Pym | |
| 297 | OH | 4-O-C(=N-OCH₃)(=N-OCH₃) | 2-S-Pym | |
| 298 | OCH₃ | 4-Ph | 2-S-Tri | |
| 299 | OH | 4-Ph | 2-S-Tri | 146~147.5 |
| 300 | OC₂H₅ | 4-phenyl-Cl | 2-S-Pym | 89~98 |

TABLE 1-continued

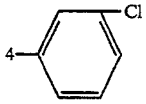

| Compound No. | R | Xn | A | Physical properties Melting point (°C.) or Refractive index ($n_D^{20}$) |
|---|---|---|---|---|
| 301 | NHSO₂CH₃ | 4-Cl-C₆H₄ | 2-S-Pym | 54~58 |
| 302 | 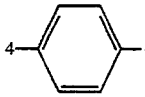 | 4-Cl-C₆H₄ | 2-S-Pym | 54~61 |
| 303 | 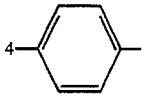 | 4-Cl-C₆H₄ | 2-S-Pym | unmeasurable |
| 304 | SCH₃ | 4-Cl-C₆H₄ | 2-S-Pym | 131~132 |
| 305 | O-Ph | 4-Cl-C₆H₄ | 2-S-Pym | unmeasurable |
| 306 | S-Ph | 4-Cl-C₆H₄ | 2-S-Pym | |
| 307 | O⁻Na⁺ | 4-Cl-C₆H₄ | 2-S-Pym | 244~247 |
| 308 | OCH(CH₃)—OCOC₄H₉-t | 4-Cl-C₆H₄ | 2-S-Pym | |
| 309 | OCH₃ | 4-Ph | (i) | |
| 310 | OH | 4-Ph | (i) | 137~141 |
| 311 | OCH(CH₃)—OCOC₄H₉-t | 4-OCHF₂-C₆H₄ | 2-S-Pym | |
| 312 | OH | 4-OCHF₂-C₆H₄ | 2-S-Pym | |
| 313 | OCH₂OCOC₄H₉-t | 4-N(CH₃)₂-C₆H₄ | 2-S-Pym | |

TABLE 1-continued
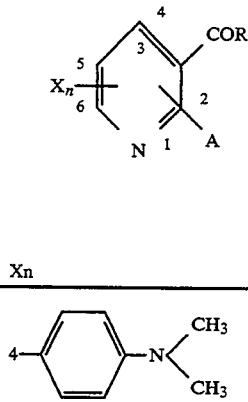
| Compound No. | R | Xn | A | Physical properties Melting point (°C.) or Refractive index ($n_D^{20}$) |
|---|---|---|---|---|
| 314 | OH | 4-—C₆H₄—N(CH₃)₂ | 2-S-Pym | 173~177 |
| 315 | OCH₃ | 4-(4-CH₃O-C₆H₄) | 2-S-Pym | 1.5938 |
| 316 | OH | 4-(4-CH₃O-C₆H₄) | 2-S-Pym | 189~192 |
| 317 | OCH₂OCH₃ | 4-(4-CH₃O-C₆H₄) | 2-O-Pym | |
| 318 | OH | 4-(4-CH₃O-C₆H₄) | 2-O-Pym | |
| 319 | OCH₂OCOC₄H₉-t | 4-(3-OCH₃-C₆H₄) | 2-S-Pym | |
| 320 | OH | 4-(3-OCH₃-C₆H₄) | 2-S-Pym | 187.5~189 |
| 321 | OCH₂OCOC₄H₉-t | 4-(3-OCH₃-C₆H₄) | 2-O-Pym | |
| 322 | OH | 4-(3-OCH₃-C₆H₄) | 2-O-Pym | |
| 323 | OCH(CH₃)OCOC₄H₉-t | 4-(3-OC₃H₇-C₆H₄) | 2-S-Pym | |
| 324 | OH | 4-(3-OC₃H₇-C₆H₄) | 2-S-Pym | |

TABLE 1-continued

[Structure: pyridine-like ring with positions 1(N), 2(A), 3(COR), 4, 5, 6, with X$_n$ substituent]

| Compound No. | R | Xn | A | Physical properties Melting point (°C.) or Refractive index ($n_D^{20}$) |
|---|---|---|---|---|
| 325 | OCH$_2$OCOC$_4$H$_9$-t | 4-(phenyl with OC$_3$H$_7$-i) | 2-S-Pym | |
| 326 | OH | 4-(phenyl with OC$_3$H$_7$-i) | 2-S-Pym | |
| 327 | OCH$_2$OCOC$_4$H$_9$-t | 4-(phenyl with O-Ph) | 2-S-Pym | |
| 328 | OH | 4-(phenyl with O-Ph) | 2-S-Pym | |
| 329 | OCH$_3$ | 4-(phenyl-O-phenyl-CH$_3$) | 2-S-Pym | |
| 330 | OH | 4-(phenyl-O-phenyl-CH$_3$) | 2-S-Pym | |
| 331 | OCH$_2$OCOC$_4$H$_9$-t | 4-Ph, 5-OCH$_3$ | 2-O-Pym | |
| 332 | OH | 4-Ph, 5-OCH$_3$ | 2-O-Pym | |
| 333 | OCH$_2$OCOC$_4$H$_9$-t | 4-Ph, 5-CH$_3$ | 2-O-Pym | |
| 334 | OH | 4-(phenyl with OCH$_2$OCH$_3$) | 2-S-Pym | |
| 335 | OCH$_2$OCOC$_4$H$_9$-t | 4-Ph, 5-Cl | 2-O-Pym | |
| 336 | OH | 4-Ph, 5-Cl | 2-O-Pym | |
| 337 | OCH(CH$_3$)—OCOC$_4$H$_9$-t | 4-Ph, 5-Cl | 2-S-Pym | |
| 338 | OH | 4-Ph, 5-Cl | 2-S-Pym | |
| 339 | OCH$_2$OCOC$_4$H$_9$-t | 4-Ph, 5-N(CH$_3$)$_2$ | 2-S-Pym | |
| 340 | OH | 4-Ph, 5-N(CH$_3$)$_2$ | 2-S-Pym | |
| 341 | OCH$_2$OCH$_3$ | 4-Ph, 5-N(CH$_3$)$_2$ | 2-O-Pym | |

TABLE 1-continued

| Compound No. | R | Xn | A | Physical properties Melting point (°C.) or Refractive index ($n_D^{20}$) |
|---|---|---|---|---|
| 342 | OH | 4-Ph, 5-N(CH₃)(CH₃) | 2-O-Pym | |
| 343 | OCH(CH₃)OCOC₄H₉-t | 4-Ph, 6-Cl | 2-O-Pym | |
| 344 | OH | 4-Ph, 6-Cl | 2-O-Pym | |
| 345 | OCH₂OCOC₄H₉-t | 4-Ph, 6-Cl | 2-S-Pym | |
| 346 | OH | 4-Ph, 6-Cl | 2-S-Pym | |
| 347 | OCH₂OCOC₄H₉-t | 4-Ph, 6-OCH₃ | 2-S-Pym | |
| 348 | OH | 4-Ph, 6-OCH₃ | 2-S-Pym | |
| 349 | OCH₂OC₂H₅ | 4-Ph, 6-OCH₃ | 2-O-Pym | |
| 350 | OH | 4-Ph, 6-OCH₃ | 2-O-Pym | |
| 351 | OCH₂OCOC₄H₉-t | 4-Ph, 6-N(CH₃)(CH₃) | 2-O-Pym | |
| 352 | OH | 4-Ph, 6-N(CH₃)(CH₃) | 2-O-Pym | |
| 353 | OCH(CH₃)OCOC₄H₉-t | 4-Ph, 6-N(CH₃)(CH₃) | 2-S-Pym | |
| 354 | OH | 4-Ph, 6-N(CH₃)(CH₃) | 2-S-Pym | |
| 355 | OCH₂OCOC₄H₉-t | 4-Ph, 6-C₂H₅ | 2-S-Pym | |
| 356 | OH | 4-Ph, 6-C₂H₅ | 2-S-Pym | |
| 357 | OCH₂OCOC₄H₉-t | 4-Ph, 6-C₂H₅ | 2-O-Pym | |
| 358 | OH | 4-Ph, 6-C₂H₅ | 2-O-Pym | |
| 359 | OH | 4-(C₆H₄-OCHF₂) | 2-O-Pym | |
| 360 | OCH₂OCOC₄H₉-t | 4-(C₆H₄-OCHF₂) | 2-O-Pym | |
| 361 | OH | 4-(C₆H₄-OCHF₂) | 2-S-Pym | |
| 362 | OH | 4-(C₆H₄-OCHF₂) | 2-O-Pym | |

TABLE 1-continued
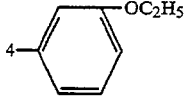
| Compound No. | R | Xn | A | Physical properties Melting point (°C.) or Refractive index ($n_D^{20}$) |
|---|---|---|---|---|
| 363 | OCH$_2$OCOC$_4$H$_9$-t | 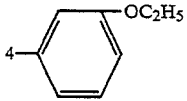 4-OC$_2$H$_5$ | 2-O-Pym | |
| 364 | OH | 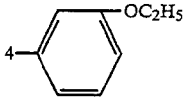 4-OC$_2$H$_5$ | 2-O-Pym | |
| 365 | OH | 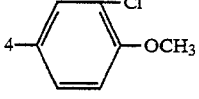 4-OC$_2$H$_5$ | 2-S-Pym | |
| 366 | OH | 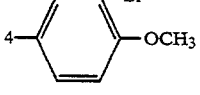 4-Cl, OCH$_3$ | 2-S-Pym | |
| 367 | OH | 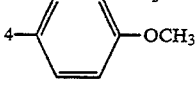 4-Br, OCH$_3$ | 2-S-Pym | |
| 368 | OH | 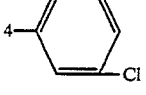 4-CH$_3$, OCH$_3$ | 2-S-Pym | |
| 369 | OH | 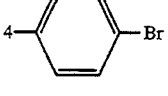 4-Cl, Cl | 2-S-Pym | |
| 370 | OH | 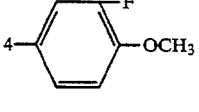 4-Br, Br | 2-S-Pym | |
| 371 | OH | 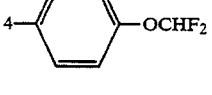 4-F, OCH$_3$ | 2-S-Pym | |
| 372 | OH | 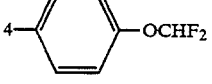 4-Cl, OCHF$_2$ | 2-S-Pym | |
| 373 | OH | 4-CHF$_2$, OCHF$_2$ | 2-S-Pym | |

TABLE 1-continued $$X_n \underset{6}{\overset{5}{\bigodot}} \underset{N}{\overset{4}{\underset{1}{\bigodot}}} \overset{COR}{\underset{A}{\bigodot}}$$

| Compound No. | R | Xn | A | Physical properties Melting point (°C.) or Refractive index ($n_D^{20}$) |
|---|---|---|---|---|
| 374 | OH | 4- (2,6-diCl, OCH₃) phenyl | 2-S-Pym | |
| 375 | -N(imidazolyl) | 4-(4-Cl)phenyl | 2-S-Pym | 145.5~147 |
| 376 | OH | 4-(3-OCH₃, 4-Br)phenyl | 2-S-Pym | |
| 377 | OH | 4-Ph | (j) | |
| 378 | OH | 4-Ph | (k) | |
| 379 | OH | 4-Ph | (l) | |
| 380 | OH | H | 2-S-Tri | |
| 381 | OH | 4-(3-CN)phenyl | 2-S-Pym | |
| 382 | OH | 4-(3-C≡CH)phenyl | 2-S-Pym | |
| 383 | OH | 4-(4-NHCH₃)phenyl | 2-S-Pym | |
| 384 | OH | 4-(4-OCH₂COOC₂H₅)phenyl | 2-S-Pym | |
| 385 | OH | 4-(4-OCH(CH₃)COOC₂H₅, 3-CH₃)phenyl | 2-S-Pym | |
| 386 | OH | 4-(2-Br, 3-CH₂OCH₃)phenyl | 2-S-Pym | |
| 387 | OH | 4-(2-Br, 3-CH₂OCH₃)phenyl | 2-S-Pym | |

TABLE 1-continued

Structure: pyridine ring with positions 1(N), 2(A), 3(COR attached via C=C), 4, 5, 6; Xn on the benzene/pyridine ring at positions 5,6.

| Compound No. | R | Xn | A | Physical properties Melting point (°C.) or Refractive index ($n_D^{20}$) |
|---|---|---|---|---|
| 388 | OH | 4-(Br, OCH$_2$CH$_2$OCH$_3$)phenyl | 2-S-Pym | |
| 389 | OH | 4-(Br, OCH$_2$OC$_2$H$_5$)phenyl | 2-S-Pym | |
| 390 | OH | 4-(Br, OCH$_2$SCH$_3$)phenyl | 2-S-Pym | |
| 391 | OH | 4-(Br, OCH$_2$COC$_2$H$_5$)phenyl | 2-S-Pym | |
| 392 | OH | 4-(OC$_2$H$_5$, OCH$_3$)phenyl | 2-S-Pym | |
| 393 | OH | 4-(NHC$_3$H$_7$, OCH$_3$)phenyl | 2-S-Pym | |
| 394 | OH | 4-(Br, OCH$_2$CH$_2$SCH$_3$)phenyl | 2-S-Pym | |
| 395 | OH | 4-(Br, OCH$_2$SC$_2$H$_5$)phenyl | 2-S-Pym | |
| 396 | OH | 4-(Br, OH)phenyl | 2-S-Pym | |
| 397 | OH | 4-(Br, OCH$_2$-Ph)phenyl | 2-S-Pym | |
| 398 | OCH$_2$-Ph | H | (j) | 128~131 |
| 399 | OCH$_2$-Ph | H | (k) | |
| 400 | OCH$_2$-Ph | H | (l) | 1.5634 |
| 401 | OCH$_3$ | 4-OCH$_3$ phenyl | 2-S-Pym | 1.5901 |

TABLE 1-continued

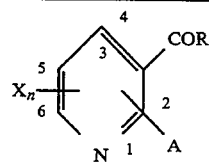

| Compound No. | R | Xn | A | Physical properties Melting point (°C.) or Refractive index ($n_D^{20}$) |
|---|---|---|---|---|
| 402 | OCH$_3$ | 4-(C$_6$H$_4$)-OCH$_3$ | 2-O-Pym | 1.5611 |
| 403 | OH | 4-(C$_6$H$_4$)-OCH$_2$OC$_2$H$_5$ | 2-S-Pym | |
| 404 | OH | 4-(C$_6$H$_4$)-OCH$_2$OC$_2$H$_5$ | 2-S-Pym | |
| 405 | O$^-$N$^+$H$_3$C$_3$H$_7$-i | 4-(C$_6$H$_4$)-Cl | 2-S-Pym | 161~168 |
| 406 | OH | H | 2-S-Pym | 123~124 |
| 407 | OH | 4-SCH$_2$-Ph | 2-S-Pym | 138~144 |
| 408 | OH | 4-OCHF$_2$ | 2-S-Pym | |
| 409 | OH | 4-Ph | (m) | 202~205 |
| 410 | OH | 4-OCH$_2$-Ph | 2-S-Pym | |
| 411 | OH | 4-OCH$_2$CH=CH$_2$ | 2-S-Pym | |
| 412 | OH | 4-OCH$_2$C≡CH | 2-S-Pym | |
| 413 | OH | 4-(cyclopentyl) | 2-S-Pym | |
| 414 | OH | 5-Ph | 2-S-Pym | |
| 415 | OH | 6-Ph | 2-S-Pym | |
| 416 | OCH$_2$OCO-Ph | 4-Ph | 2-S-Pym | |
| 417 | OH | 4-NHCO-Ph | 2-S-Pym | |
| 418 | OCH$_3$ | 4-SCH$_2$-Ph | 2-S-Pym | 81~86 |

TABLE 2

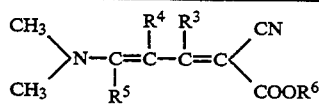

| Intermediate No. | R$^3$ | R$^4$ | R$^5$ | R$^6$ | Physical properties Melting point (°C.) or Refractive index ($n_D^{20}$) |
|---|---|---|---|---|---|
| 1 | Ph— | H | H | CH$_3$ | 144~146 |
| 2 | Ph— | H | H | C$_2$H$_5$ | |
| 3 | 4-CH$_3$-C$_6$H$_4$— | H | H | CH$_3$ | |

TABLE 2-continued $$\underset{CH_3}{\overset{CH_3}{N}}-\underset{R^5}{\overset{R^4}{C}}=\underset{}{\overset{R^3}{C}}-\underset{COOR^6}{\overset{CN}{C}}$$

| Intermediate No. | $R^3$ | $R^4$ | $R^5$ | $R^6$ | Physical properties Melting point (°C.) or Refractive index ($n_D^{20}$) |
|---|---|---|---|---|---|
| 4 | 4-Cl-C$_6$H$_4$— | H | H | CH$_3$ | |
| 5 | 4-CH$_3$O-C$_6$H$_4$— | H | H | CH$_3$ | 175~178 |
| 6 | 2-Cl-C$_6$H$_4$— | H | H | CH$_3$ | 164~166.5 |
| 7 | 3-Cl-C$_6$H$_4$— | H | H | CH$_3$ | 156~159 |
| 8 | Ph— | CH$_3$ | H | CH$_3$ | |
| 9 | Ph— | H | CH$_3$ | CH$_3$ | 180~184 |
| 10 | CH$_3$O— | H | H | CH$_3$ | 125~128 |
| 11 | CH$_3$— | H | H | CH$_3$ | 88~93 |
| 12 | (CH$_3$)$_2$N— | H | H | CH$_3$ | 121~126 |
| 13 | CH$_3$NH— | H | H | CH$_3$ | |
| 14 | 4-CH$_3$-C$_6$H$_4$— | H | CH$_3$ | CH$_3$ | |
| 15 | i-C$_3$H$_7$— | H | H | CH$_3$ | 123~126 |
| 16 | i-C$_3$H$_7$— | H | CH$_3$ | CH$_3$ | |
| 17 | 3-CH$_3$-C$_6$H$_4$— | H | H | CH$_3$ | 136~140 |
| 18 | 3,4-(CH$_3$)$_2$-C$_6$H$_3$— | H | H | CH$_3$ | 183.5~188 |
| 19 | 4-F-C$_6$H$_4$— | H | H | CH$_3$ | 198.5~200.5 |
| 20 | 2-F-C$_6$H$_4$— | H | H | CH$_3$ | 215~217.5 |

TABLE 2-continued $$\begin{array}{c}CH_3\\ \phantom{CH_3}\diagdown\\ \phantom{CH_3}N-\underset{\underset{R^5}{|}}{C}=\underset{}{\overset{R^4}{C}}-\underset{}{\overset{R^3}{C}}=C\diagup\underset{COOR^6}{\overset{CN}{}}\\ CH_3\diagup\end{array}$$

| Intermediate No. | $R^3$ | $R^4$ | $R^5$ | $R^6$ | Physical properties Melting point (°C.) or Refractive index ($n_D^{20}$) |
|---|---|---|---|---|---|
| 21 | 2-F-C$_6$H$_4$ | H | H | CH$_3$ | 157~159 |
| 22 | 3-CH$_3$O-C$_6$H$_4$ | H | H | CH$_3$ | 159~162 |
| 23 | 2-CH$_3$O-C$_6$H$_4$ | H | H | CH$_3$ | 122~126 |
| 24 | 3,4-(CH$_3$O)$_2$-C$_6$H$_3$ | H | H | CH$_3$ | 205~208 |
| 25 | 4-Br-C$_6$H$_4$ | H | H | CH$_3$ | 219~223 |
| 26 | 3-Br-C$_6$H$_4$ | H | H | CH$_3$ | 180~184 |
| 27 | 4-C$_2$H$_5$O-C$_6$H$_4$ | H | H | CH$_3$ | 148~150 |
| 28 | 3-C$_2$H$_5$O-C$_6$H$_4$ | H | H | CH$_3$ | |
| 29 | 4-C$_3$H$_7$O-C$_6$H$_4$ | H | H | CH$_3$ | 147~149 |
| 30 | 4-i-C$_3$H$_7$O-C$_6$H$_4$ | H | H | CH$_3$ | 154~157 |
| 31 | 3-i-C$_3$H$_7$O-C$_6$H$_4$ | H | H | CH$_3$ | |
| 32 | 4-CHF$_2$O-C$_6$H$_4$ | H | H | CH$_3$ | |

TABLE 2-continued $$\underset{CH_3}{\overset{CH_3}{N}}-\underset{R^5}{\overset{R^4}{C}}=\underset{}{\overset{R^3}{C}}-\underset{}{\overset{}{C}}=\underset{COOR^6}{\overset{CN}{C}}$$

| Intermediate No. | R³ | R⁴ | R⁵ | R⁶ | Physical properties Melting point (°C.) or Refractive index ($n_D^{20}$) |
|---|---|---|---|---|---|
| 33 | CHF₂O—C₆H₄— | H | H | CH₃ | |
| 34 | 4-(CH₃)₂N—C₆H₄— | H | H | CH₃ | |
| 35 | 3-(CH₃)₂N—C₆H₄— | H | H | CH₃ | |
| 36 | 4-(piperidino)—C₆H₄— | H | H | CH₃ | 149~152 |
| 37 | C₂H₅—C₆H₄— | H | H | CH₃ | 127~130 |
| 38 | 4-C₃H₇—C₆H₄— | H | H | CH₃ | 129~131 |
| 39 | 3,4-F₂—C₆H₃— | H | H | CH₃ | 232~233.5 |
| 40 | 4-i-C₃H₇—C₆H₄— | H | H | CH₃ | 184~187 |
| 41 | 3-i-C₃H₇—C₆H₄— | H | H | CH₃ | |
| 42 | 4-CF₃—C₆H₄— | H | H | CH₃ | 225~227 |
| 43 | 3-CF₃—C₆H₄— | H | H | CH₃ | |
| 44 | 3-NO₂—C₆H₄— | H | H | CH₃ | |

TABLE 2-continued $$\text{(CH}_3\text{)}_2\text{N-C(R}^5\text{)=C(R}^4\text{)-C(R}^3\text{)=C(CN)(COOR}^6\text{)}$$

| Intermediate No. | R³ | R⁴ | R⁵ | R⁶ | Physical properties Melting point (°C.) or Refractive index ($n_D^{20}$) |
|---|---|---|---|---|---|
| 45 | 2-CH₃-C₆H₄— | H | H | CH₃ | 155.5~157 |
| 46 | 4-CH₃S-C₆H₄— | H | H | CH₃ | |
| 47 | Ph—O— | H | H | CH₃ | 195~198 |
| 48 | 3-CH₃-4-Cl-C₆H₃— | H | H | CH₃ | 183~185.5 |
| 49 | Ph— | OCH₃ | H | CH₃ | 154~158 |
| 50 | 4-Br-C₆H₄— | H | CH₃ | CH₃ | 198~201 |
| 51 | 4-C₃H₇-C₆H₄— | H | CH₃ | CH₃ | 131~136 |
| 52 | 4-F-C₆H₄— | H | CH₃ | CH₃ | 190~192.5 |

TABLE 3

$$\text{pyridine with R}^3, R^4, R^5, \text{COOR}^6, \text{OH}$$

| Intermediate No. | R³ | R⁴ | R⁵ | R⁶ | Physical properties Melting point (°C.) or Refractive index ($n_D^{20}$) |
|---|---|---|---|---|---|
| 53 | Ph— | H | H | CH₃ | 172~178 |
| 54 | Ph— | H | H | C₂H₅ | |
| 55 | 4-CH₃-C₆H₄— | H | H | CH₃ | 248~251 |
| 56 | 4-Cl-C₆H₄— | H | H | CH₃ | 186~190 |

TABLE 3-continued

Structure: pyridine with R³ at 4-position, R⁴ at 5-position, R⁵ at 6-position, COOR⁶ at 3-position, and 2-OH

| Intermediate No. | R³ | R⁴ | R⁵ | R⁶ | Physical properties Melting point (°C.) or Refractive index ($n_D^{20}$) |
|---|---|---|---|---|---|
| 57 | 4-CH₃O-C₆H₄- | H | H | CH₃ | 214~220 |
| 58 | 2-Cl-C₆H₄- | H | H | CH₃ | 200~206 |
| 59 | 3-Cl-C₆H₄- | H | H | CH₃ | 228~235 |
| 60 | Ph— | CH₃ | H | CH₃ | |
| 61 | Ph— | H | CH₃ | CH₃ | 185~190 |
| 62 | CH₃O— | H | H | CH₃ | 186~191 |
| 63 | CH₃— | H | H | CH₃ | 151~155 |
| 64 | (CH₃)₂N— | H | H | CH₃ | 181~185 |
| 65 | CH₃NH— | H | H | CH₃ | |
| 66 | 4-CH₃-C₆H₄- | H | CH₃ | CH₃ | 222~224 |
| 67 | i-C₃H₇— | H | H | CH₃ | 138~140.5 |
| 68 | i-C₃H₇— | H | CH₃ | CH₃ | |
| 69 | 3-CH₃-C₆H₄- | H | H | CH₃ | |
| 70 | 3,4-(CH₃)₂-C₆H₃- | H | H | CH₃ | 233~237 |
| 71 | 2-CH₃-C₆H₄- | H | H | CH₃ | |
| 72 | 4-CH₃O-C₆H₄- | H | H | CH₃ | |
| 73 | 3-CH₃O-C₆H₄- | H | H | CH₃ | |

TABLE 3-continued
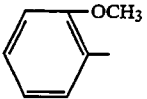
| Intermediate No. | R³ | R⁴ | R⁵ | R⁶ | Physical properties Melting point (°C.) or Refractive index (n$_D^{20}$) |
|---|---|---|---|---|---|
| 74 | 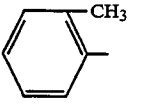 | H | H | CH₃ | |
| 75 | 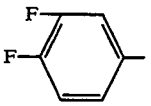 | H | H | CH₃ | |
| 76 | 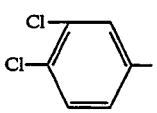 | H | H | CH₃ | |
| 77 | 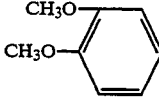 | H | H | CH₃ | |
| 78 | 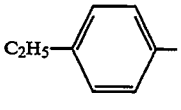 | H | H | CH₃ | 215~217.5 |
| 79 | 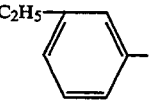 | H | H | CH₃ | |
| 80 | 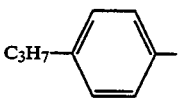 | H | H | CH₃ | |
| 81 | 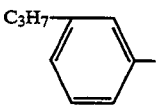 | H | H | CH₃ | |
| 82 | 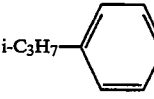 | H | H | CH₃ | |
| 83 | 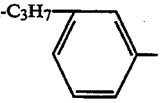 | H | H | CH₃ | |
| 84 | i-C₃H₇-⌬- | H | H | CH₃ | |

TABLE 3-continued
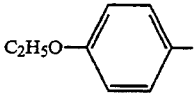
| Intermediate No. | R³ | R⁴ | R⁵ | R⁶ | Physical properties Melting point (°C.) or Refractive index ($n_D^{20}$) |
|---|---|---|---|---|---|
| 85 | 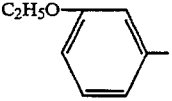 4-C₂H₅O-C₆H₄- | H | H | CH₃ | |
| 86 | 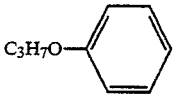 3-C₂H₅O-C₆H₄- | H | H | CH₃ | |
| 87 | 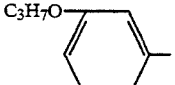 4-C₃H₇O-C₆H₄- | H | H | CH₃ | |
| 88 | 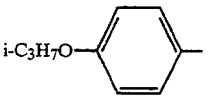 3-C₃H₇O-C₆H₄- | H | H | CH₃ | |
| 89 | 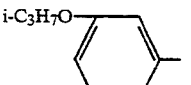 4-i-C₃H₇O-C₆H₄- | H | H | CH₃ | |
| 90 | 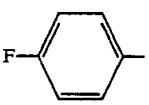 3-i-C₃H₇O-C₆H₄- | H | H | CH₃ | |
| 91 | 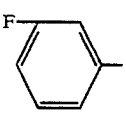 4-F-C₆H₄- | H | H | CH₃ | 214~218 |
| 92 | 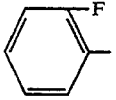 3-F-C₆H₄- | H | H | CH₃ | |
| 93 | 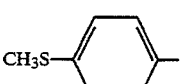 2-F-C₆H₄- | H | H | CH₃ | |
| 94 | 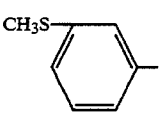 4-CH₃S-C₆H₄- | H | H | CH₃ | |
| 95 | 3-CH₃S-C₆H₄- | H | H | CH₃ | |

TABLE 3-continued

[Structure: pyridine ring with R³ at 4-position, R⁴ at 5-position, R⁵ at 6-position, COOR⁶ at 3-position, OH at 2-position, N in ring]

| Intermediate No. | R³ | R⁴ | R⁵ | R⁶ | Physical properties Melting point (°C.) or Refractive index ($n_D^{20}$) |
|---|---|---|---|---|---|
| 96 | 2-(SCH₃)C₆H₄— | H | H | CH₃ | |
| 97 | 4-(NO₂)C₆H₄— | H | H | CH₃ | |
| 98 | 3-(NO₂)C₆H₄— | H | H | CH₃ | |
| 99 | 4-(CF₃)C₆H₄— | H | H | CH₃ | |
| 100 | 3-(CF₃)C₆H₄— | H | H | CH₃ | |
| 101 | 3-Cl-4-CH₃-C₆H₃— | H | H | CH₃ | |
| 102 | 4-(N(CH₃)₂)C₆H₄— | H | H | CH₃ | |
| 103 | 3-(N(CH₃)₂)C₆H₄— | H | H | CH₃ | |
| 104 | 4-(CHF₂O)C₆H₄— | H | H | CH₃ | |
| 105 | 3-(CHF₂O)C₆H₄— | H | H | CH₃ | |
| 106 | 4-Br-C₆H₄— | H | H | CH₃ | 240~242 |

TABLE 3-continued

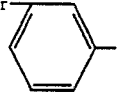

| Intermediate No. | R³ | R⁴ | R⁵ | R⁶ | Physical properties Melting point (°C.) or Refractive index (n_D^20) |
|---|---|---|---|---|---|
| 107 | Br-C₆H₄- | H | H | CH₃ | 235~239 |
| 108 | i-C₃H₇-C₆H₄- | H | H | CH₃ | |
| 109 | Br-C₆H₄- | H | CH₃ | CH₃ | 196~200 |
| 110 | C₂H₅-C₆H₄- | H | CH₃ | CH₃ | 192~197 |

TABLE 4

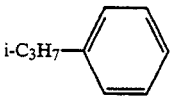

| Intermediate No. | R³ | R⁴ | R⁵ | R⁶ | L | Physical properties Melting point (°C.) or Refractive index (n_D^20) |
|---|---|---|---|---|---|---|
| 111 | Ph— | H | H | CH₃ | Br | |
| 112 | Ph— | H | H | H | Cl | 190~194 |
| 113 | Ph— | H | H | H | Br | 181~184 |
| 114 | Cl-C₆H₄- | H | H | CH₃ | Br | 73~76 |
| 115 | Cl-C₆H₄- | H | H | H | Br | 204~208 |
| 116 | Cl-C₆H₄- | H | H | H | Cl | 209~212 |
| 117 | Cl-C₆H₄- | H | H | CH₃ | Br | |

TABLE 4-continued $$\underset{R^5}{\overset{R^4}{\phantom{X}}}\underset{N}{\overset{R^3}{\bigcirc}}\overset{COOR^6}{\underset{L}{\phantom{X}}}$$

| Intermediate No. | R³ | R⁴ | R⁵ | R⁶ | L | Physical properties Melting point (°C.) or Refractive index ($n_D^{20}$) |
|---|---|---|---|---|---|---|
| 118 | 4-Cl-C₆H₄- | H | H | H | Br | 178~182 |
| 119 | 2-Cl-C₆H₄- | H | H | CH₃ | Br | |
| 120 | 2-Cl-C₆H₄- | H | H | H | Br | 183~186.5 |
| 121 | 4-CH₃-C₆H₄- | H | H | CH₃ | Cl | |
| 122 | 4-CH₃-C₆H₄- | H | H | H | Cl | 195~199 |
| 123 | 3-CH₃-C₆H₄- | H | H | CH₃ | Br | |
| 124 | 3-CH₃-C₆H₄- | H | H | H | Br | 180~182 |
| 125 | 2-CH₃-C₆H₄- | H | H | CH₃ | Br | 166~169 |
| 126 | 2-CH₃-C₆H₄- | H | H | H | Br | |
| 127 | 4-CH₃O-C₆H₄- | H | H | CH₃ | Br | 89~90.5 |
| 128 | 4-CH₃O-C₆H₄- | H | H | H | Br | 206~209 |

TABLE 4-continued
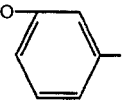
| Intermediate No. | R³ | R⁴ | R⁵ | R⁶ | L | Physical properties Melting point (°C.) or Refractive index (n_D^{20}) |
|---|---|---|---|---|---|---|
| 129 | 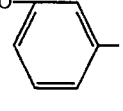 3-CH₃O-C₆H₄ | H | H | CH₃ | Br | |
| 130 | 3-CH₃O-C₆H₄ | H | H | H | Br | |
| 131 | 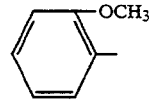 2-OCH₃-C₆H₄ | H | H | CH₃ | Br | |
| 132 | 2-OCH₃-C₆H₄ | H | H | H | Br | |
| 133 | 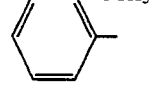 4-F-C₆H₄ | H | H | CH₃ | Br | 79~82 |
| 134 | 4-F-C₆H₄ | H | H | H | Br | |
| 135 | 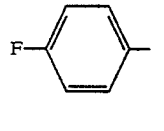 3-F-C₆H₄ | H | H | CH₃ | Br | |
| 136 | 3-F-C₆H₄ | H | H | H | Br | 197~199.5 |
| 137 | 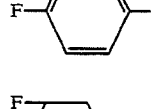 2-F-C₆H₄ | H | H | CH₃ | Br | 71~73 |
| 138 | 2-F-C₆H₄ | H | H | H | Br | 165~168.5 |
| 139 | 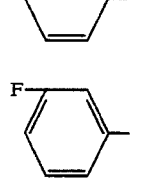 4-Br-C₆H₄ | H | H | CH₃ | Br | |

TABLE 4-continued
$$\text{structure with } R^3, R^4, R^5, \text{COOR}^6, L, N$$
| Intermediate No. | R³ | R⁴ | R⁵ | R⁶ | L | Physical properties Melting point (°C.) or Refractive index ($n_D^{20}$) |
|---|---|---|---|---|---|---|
| 140 | 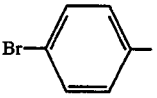 4-Br-C₆H₄- | H | H | H | Br | 215~219 |
| 141 | 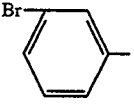 3-Br-C₆H₄- | H | H | CH₃ | Br | 85.5~87 |
| 142 | 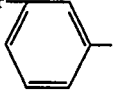 3-Br-C₆H₄- | H | H | H | Br | 185~189 |
| 143 | 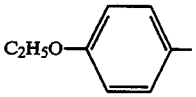 4-C₂H₅O-C₆H₄- | H | H | CH₃ | Br | 83~84.5 |
| 144 | 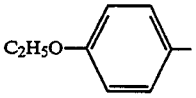 4-C₂H₅O-C₆H₄- | H | H | H | Br | 180~184 |
| 145 | 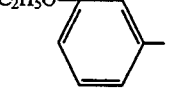 3-C₂H₅O-C₆H₄- | H | H | CH₃ | Br | |
| 146 | 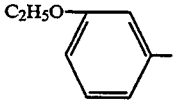 3-C₂H₅O-C₆H₄- | H | H | H | Br | |
| 147 | 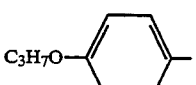 4-C₃H₇O-C₆H₄- | H | H | CH₃ | Br | |
| 148 | 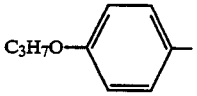 4-C₃H₇O-C₆H₄- | H | H | H | Br | |
| 149 | 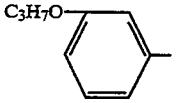 3-C₃H₇O-C₆H₄- | H | H | CH₃ | Br | |
| 150 | 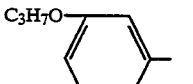 3-C₃H₇O-C₆H₄- | H | H | H | Br | |

TABLE 4-continued $$\underset{R^5}{\overset{R^4}{\underset{N}{\bigvee}}}\overset{R^3}{\underset{L}{\bigvee}}COOR^6$$

| Intermediate No. | R³ | R⁴ | R⁵ | R⁶ | L | Physical properties Melting point (°C.) or Refractive index ($n_D^{20}$) |
|---|---|---|---|---|---|---|
| 151 | i-C₃H₇O—⟨phenyl⟩— | H | H | CH₃ | Br | 168~173 |
| 152 | i-C₃H₇O—⟨phenyl⟩— | H | H | H | Br | 163~167 |
| 153 | i-C₃H₇O—⟨phenyl⟩— | H | H | CH₃ | Br | |
| 154 | i-C₃H₇O—⟨phenyl⟩— | H | H | H | Br | |
| 155 | C₂H₅—⟨phenyl⟩— | H | H | CH₃ | Br | 73~75 |
| 156 | C₂H₅—⟨phenyl⟩— | H | H | H | Br | 160~163 |
| 157 | C₂H₅—⟨phenyl⟩— | H | H | CH₃ | Br | |
| 158 | C₂H₅—⟨phenyl⟩— | H | H | H | Br | |
| 159 | C₃H₇—⟨phenyl⟩— | H | H | H | Br | 69~73 |
| 160 | C₃H₇—⟨phenyl⟩— | H | H | CH₃ | Br | |
| 161 | C₃H₇—⟨phenyl⟩— | H | H | CH₃ | Br | |

TABLE 4-continued
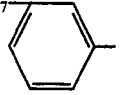
| Intermediate No. | R³ | R⁴ | R⁵ | R⁶ | L | Physical properties Melting point (°C.) or Refractive index (n$_D^{20}$) |
|---|---|---|---|---|---|---|
| 162 | C₃H₇—⟨phenyl⟩— | H | H | H | Br | |
| 163 | i-C₃H₇—⟨phenyl⟩— | H | H | CH₃ | Br | |
| 164 | i-C₃H₇—⟨phenyl⟩— | H | H | H | Br | 173~176 |
| 165 | i-C₃H₇—⟨phenyl⟩— | H | H | CH₃ | Br | |
| 166 | i-C₃H₇—⟨phenyl⟩— | H | H | H | Br | |
| 167 | NO₂—⟨phenyl⟩— | H | H | CH₃ | Br | |
| 168 | NO₂—⟨phenyl⟩— | H | H | H | Br | 193~197 |
| 169 | NO₂—⟨phenyl⟩— | H | H | CH₃ | Br | |
| 170 | NO₂—⟨phenyl⟩— | H | H | H | Br | |
| 171 | CF₃—⟨phenyl⟩— | H | H | CH₃ | Br | |
| 172 | CF₃—⟨phenyl⟩— | H | H | H | Br | 188~191 |

TABLE 4-continued

Structure: pyridine with R³ at 4-position, R⁴ at 5-position, R⁵ at 6-position, COOR⁶ at 3-position, L at 2-position

| Intermediate No. | R³ | R⁴ | R⁵ | R⁶ | L | Physical properties Melting point (°C.) or Refractive index ($n_D^{20}$) |
|---|---|---|---|---|---|---|
| 173 | 3-CF₃-C₆H₄- | H | H | CH₃ | Br | |
| 174 | 3-CF₃-C₆H₄- | H | H | H | Br | |
| 175 | 4-CHF₂O-C₆H₄- | H | H | CH₃ | Br | |
| 176 | 4-CHF₂O-C₆H₄- | H | H | H | Br | |
| 177 | 3-CHF₂O-C₆H₄- | H | H | CH₃ | Br | |
| 178 | 3-CHF₂O-C₆H₄- | H | H | H | Br | |
| 179 | 3,4-F₂-C₆H₃- | H | H | CH₃ | Br | 86~89 |
| 180 | 3,4-F₂-C₆H₃- | H | H | H | Br | 172~175 |
| 181 | 3,4-Cl₂-C₆H₃- | H | H | CH₃ | Br | 96~98 |
| 182 | 3,4-Cl₂-C₆H₃- | H | H | H | Br | 198~201 |
| 183 | 3,4-(CH₃)₂-C₆H₃- | H | H | CH₃ | Br | 89~92 |

TABLE 4-continued

[Structure: pyridine with R³ at 4-position, R⁴ at 5-position, R⁵ at 6-position, COOR⁶ at 3-position, L at 2-position]

| Intermediate No. | R³ | R⁴ | R⁵ | R⁶ | L | Physical properties Melting point (°C.) or Refractive index ($n_D^{20}$) |
|---|---|---|---|---|---|---|
| 184 | 3,4-(CH₃)₂-C₆H₃- | H | H | H | Br | |
| 185 | 3,4-(CH₃O)₂-C₆H₃- | H | H | CH₃ | Br | |
| 186 | 3,4-(CH₃O)₂-C₆H₃- | H | H | H | Br | 208~210 |
| 187 | 3-Cl-4-CH₃-C₆H₃- | H | H | CH₃ | Br | |
| 188 | 3-Cl-4-CH₃-C₆H₃- | H | H | H | Br | 174~177 |
| 189 | 4-(piperidin-1-yl)-C₆H₄- | H | H | CH₃ | Br | |
| 190 | 4-(piperidin-1-yl)-C₆H₄- | H | H | H | Br | |
| 191 | 4-(CH₃)₂N-C₆H₄- | H | H | CH₃ | Br | |
| 192 | 4-(CH₃)₂N-C₆H₄- | H | H | H | Br | |
| 193 | 3-(CH₃)₂N-C₆H₄- | H | H | CH₃ | Br | |
| 194 | 3-(CH₃)₂N-C₆H₄- | H | H | H | Br | |

TABLE 4-continued $$\begin{array}{c} R^4 \overset{R^3}{\underset{R^5}{\bigvee}} COOR^6 \\ \phantom{R^5}N \phantom{xx} L \end{array}$$

| Intermediate No. | $R^3$ | $R^4$ | $R^5$ | $R^6$ | L | Physical properties Melting point (°C.) or Refractive index ($n_D^{20}$) |
|---|---|---|---|---|---|---|
| 195 | 4-(CH$_3$S)C$_6$H$_4$— | H | H | CH$_3$ | Br | |
| 196 | 4-(CH$_3$S)C$_6$H$_4$— | H | H | H | Br | |
| 197 | 3-(CH$_3$S)C$_6$H$_4$— | H | H | CH$_3$ | Br | |
| 198 | 3-(CH$_3$S)C$_6$H$_4$— | H | H | H | Br | |
| 199 | Ph—O— | H | H | CH$_3$ | Br | 118~120 |
| 200 | Ph—O— | H | H | H | Br | |
| 201 | Ph— | CH$_3$ | H | CH$_3$ | Br | 129~133 |
| 202 | Ph— | CH$_3$ | H | H | Br | 216~218 |
| 203 | 4-F-C$_6$H$_4$— | H | CH$_3$ | CH$_3$ | Br | 94~97 |
| 204 | 4-F-C$_6$H$_4$— | H | CH$_3$ | H | Br | 199~201 |
| 205 | Ph— | C$_2$H$_5$ | H | CH$_3$ | Br | 129~132 |
| 206 | Ph— | C$_2$H$_5$ | H | H | Br | 173~175 |
| 207 | Ph— | CH$_3$O | H | CH$_3$ | Br | |
| 208 | Ph— | CH$_3$O | H | H | Br | 195~199 |
| 209 | i-C$_3$H$_7$— | H | H | CH$_3$ | Cl | |
| 210 | i-C$_3$H$_7$— | H | H | H | Cl | 156~158 |
| 211 | Ph— | H | CH$_3$ | CH$_3$ | Br | |
| 212 | Ph— | H | CH$_3$ | H | Br | |
| 213 | Ph—CH$_2$S— | H | H | H | Br | 165~169 |

The herbicidal composition of the present invention comprises at least one of the pyridine derivative of the general formula (I) and its salt as an effective ingredient.

The compound of the present invention can be used as it is as a herbicide, but it may be used in such an appropriate formulation as a dust, a wettable powder, an emulsifiable concentrate, a micro-particle agent or a granule agent by blending with a carrier, a surfactant, a dispersing agent or an adjuvant which may be generally used in the formulation of agricultural chemicals.

As a carrier to be used for these formulations, there may be enumerated a solid carrier such as Jeeklite, talc, bentonite, clay, kaolin, diatomaceous earth, white carbon, vermiculite, calcium carbonate, slaked lime, silica sand, ammonium sulfate or urea, or a liquid carrier such as isopropanol, xylene, cyclohexanone or methyl naphthalene.

As a surfactant and a dispersing agent, there may be enumerated, for example, a metal salt of an alkylbenzenesulfonic acid, a metal salt of a dinaphthylmethanedisulfonic acid, an alcohol-sulfuric acid ester, an alkylaryl sulfonate, a lignin sulfonate, a polyoxyethylene glycol ether, a polyoxyethylene alkyl aryl ether or a polyoxyethylene sorbitol monoalkylate. As an adjuvant, for example, carboxymethyl cellulose, polyethylene glycol or gum arabic may be enumerated.

The dust is prepared by blending the active ingredient with a powdery solid carrier. The wettable powder can be prepared by blending the active ingredient with a powdery solid carrier, a surfactant and a dispersing agent. The emulsifiable concentrate can be prepared by mixing the active ingredient with a liquid carrier, a surfactant and a dispersing agent. The granule agent can be prepared by coating a granular solid carrier with the active ingredient, together with an adjuvant, or by adding water to a solid carrier, the active ingredient and an adjuvant and extruding the mixture through apertures. The proportion of the active ingredient is optionally selected depending on its use, and it is usually from 0.01 to 20% by weight, preferably from 0.1 to 10% by weight, in the cases of dust and granule formulations, and from 0.1 to 80% by weight, preferably from 1 to 50% by weight, in the cases of emulsifiable concentrate and wettable powder formulations.

In practical use, the herbicide of the present invention may be diluted to a suitable concentration before applying or may be directly applied. The amount of the herbicide of the present invention may be optionally varied depending on the type of the compound used, the type of weed to be controlled, growing tendency, environmental conditions and the type of formulation used. When the herbicide of the present invention is directly applied as in the case of powder and granule formulation, it is used at a dose of from 0.1 g to 5 kg, preferably from 1 g to 1 kg of the active ingredient per 10 ares. In the case of liquid application such as emulsifiable concentrate and wettable powder formulations, the active ingredient may optionally be diluted to a concentration of from 0.1 to 10,000 ppm, preferably from 10 to 5,000 ppm for application.

The herbicide of the present invention may be applied to foliage, soil or water surface.

If desired, the compound of the present invention may be used in combination with insecticides, sterilizers, other herbicides, plant growth controlling agents, fertilizers or the like.

Now, typical Formulation Examples for the herbicidal composition of the present invention will be given. The types of compounds and additives and the blending ratios should not be limited thereto, and may optionally be varied in a wide range. In these Examples, "part" means "part by weight".

FORMULATION EXAMPLE 1 (wettable powder)

10 Parts of Compound No. 4, 0.5 part of polyoxyethyleneoctylphenyl ether, 0.5 part of sodium β-naphthalenesulfonate-formalin condensate, 20 parts of diatomaceous earth and 69 parts of clay were mixed and pulverized to obtain a wettable powder.

FORMULATION EXAMPLE 2 (wettable powder)

10 Parts of Compound No. 7, 0.5 part of polyoxyethyleneoctylphenyl ether, 0.5 part of sodium β-naphthalenesulfonate-formalin condensate, 20 parts of diatomaceous earth, 5 parts of white carbon and 64 parts of clay were mixed and pulverized to obtain a wettable powder.

FORMULATION EXAMPLE 3 (wettable powder containing calcium carbonate)

10 Parts of Compound No. 23, 0.5 part of polyoxyethyleneoctylphenyl ether, 0.5 part of sodium naphthalenesulfonate-formalin condensate, 20 parts of diatomaceous earth, 5 parts of white carbon and 64 parts of calcium carbonate were mixed and pulverized to obtain a wettable powder.

FORMULATION EXAMPLE 4 (emulsifiable concentrate)

30 Parts of Compound No. 25, 60 parts of equivalent amount mixture of xylene and isophorone, and 10 parts of a surfactant mixture of polyoxyethylene sorbitol alkylate, polyoxyethylenealkylaryl polymer and alkylaryl sulfonate were fully stirred to obtain an emulsifiable concentrate.

FORMULATION EXAMPLE 5 (granule)

10 Parts of Compound No. 49, 80 parts of a bulking agent comprising a 1:3 mixture of talc and bentonite, 5 parts of white carbon, 5 parts of a surfactant mixture of polyoxyethylenesorbitol alkylate, polyoxyethylenealkylaryl polymer and alkylarylsulfonate and 10 parts of water were fully kneaded to obtain a paste-like material. The paste-like material was then extruded through a sieve aperture of 0.7 mm in diameter, and the extruded product was dried and cut into pieces of 0.5 to 1 mm in length to obtain granules.

The compound having the general formula (I) and its salt of the present invention are effective at a very small dosage for killing various troublesome weeds grown in upland fields in a wide range from germinating stage to growing stage, examples of the weeds including broadleaf weeds such as pale smartweed (*Polygonum lapathifolium*), slender amaranth (*Amaranthus viridis*), common lambsquarters (*Chenopodium album*), chickweed (*Stellaria media*), velveltleaf (*Abutilon theophrasti*), prickly sida (*Sida spinosa*), morningglory (Pomoea sp.) and common cocklebur (*Xanthum strumarium*); perennial and annual cyperaceous weeds such as purple nutsedge (*Cyperus rotundus*), yellow nutsedge, *Kyllinga brevifolia*, umbrella plant (*Cyperus microiria*) and rice flatsedge (*Cyperus iris*); and gramineous weeds such as barnyardgrass (*Echinochloa crusgalli*), crabgrass (Digitaria sp.), foxtail (Setaria sp.), annual bluegrass (*Poa annua*), johnsongrass (*Sorghum halepense*), *Alopecurus aequalis* and wild oats. Also, the compound of the present invention achieves excellent herbicidal effects on annual weeds such as barnyardgrass (*Echinochloa crusgalli*), small flower flatsedge (*Cyperus difformis*) and monochoria (*Monochoria vaginalis*), and perennial weeds such as *Sagittaria pygmaea, Cyperus serotinus, Eleocharis kuroguwai*, bulrush (*Scirpus hotarui*) and *Alisma canaliculatum*, grown in paddy fields. Depending on the type, the compound of the present invention does not have phytotoxicity to rice, wheat, cotton and corn, and is therefore suitable as a herbicide for cultivating these crops.

Now, the herbicidal effects of the compounds of the present invention will be described with reference to the following Test Examples.

TEST EXAMPLE 1

(Herbicidal effect test by paddy field soil treatment)

In a plastic pot (surface area: 100 cm$^2$) filled with paddy field soil, barnyardgrass (Ec), monochoria (Mo) and bulrush (Sc) were sown after puddling and leveling, and flooded to a water depth of 3 cm. Next day, a wettable powder prepared in accordance with Formulation Example 1 was diluted with water, and was applied dropwise to the water surface in such manner as to apply 100 g of the active ingredient per 10 ares. The plants were then cultured in a green house, and the evaluation of the herbicidal effect was conducted on the 21st day after the treatment in accordance with the standards as identified in Table 5. The results are shown in the following Table 6.

In the Test Examples, the following compounds were used as Comparative Examples. (Hereinafter, the same in each test.)

Comparative Compound A:
methyl 5-chloro-3-(4,6-dimethoxypyrimidin-2-yl)oxypicolinate (see Japanese Unexamined Patent Publication No. 84/1989)

Comparative Compound B:
N-[3-(4,6-dimethoxypyrimidin-2-yl)] trifluoromethanesulfonamide (see Japanese Unexamined Patent Publication No. 149567/1990)

TABLE 5

| Index No. | Herbicidal effects and phytotoxicity (grow-controlling degree) | |
| --- | --- | --- |
| 5 | Herbicidal effect: | at least 90% |
|   | Phytotoxicity: | at least 90% |
| 4 | Herbicidal effect: | at least 70% and less than 90% |
|   | Phytotoxicity: | at least 70% and less than 90% |
| 3 | Herbicidal effect: | at least 50% and less than 70% |
|   | Phytotoxicity: | at least 50% and less than 70% |
| 2 | Herbicidal effect: | at least 30% and less than 50% |
|   | Phytotoxicity: | at least 30% and less than 50% |
| 1 | Herbicidal effect: | at least 10% and less than 30% |
|   | Phytotoxicity: | at least 10% and less than 30% |
| 0 | Herbicidal effect: | 0 to less than 10% |
|   | Phytotoxicity: | 0 to less than 10% |

TABLE 6

| Compound No. | Herbicidal effect | | |
| --- | --- | --- | --- |
|  | Ec | Mo | Sc |
| 7 | 5 | 5 | 5 |
| 11 | 4 | 5 | 3 |
| 22 | 5 | 5 | 5 |
| 23 | 5 | 5 | 5 |
| 25 | 5 | 5 | 5 |
| 47 | 5 | 5 | 5 |
| 49 | 5 | 5 | 5 |
| 52 | 5 | 5 | 4 |
| 54 | 4 | 5 | 3 |
| 86 | 5 | 5 | 5 |
| 87 | 5 | 5 | 5 |
| 88 | 5 | 5 | 5 |
| 89 | 5 | 5 | 5 |
| 90 | 5 | 5 | 5 |
| 91 | 5 | 5 | 5 |
| 94 | 5 | 5 | 5 |
| 100 | 5 | 5 | 5 |
| 102 | 5 | 5 | 5 |
| 104 | 5 | 5 | 5 |
| 105 | 5 | 5 | 5 |
| 106 | 5 | 5 | 5 |
| 107 | 5 | 5 | 5 |
| 109 | 5 | 5 | 5 |
| 113 | 5 | 5 | 5 |
| 115 | 5 | 5 | 5 |
| 117 | 5 | 5 | 5 |
| 119 | 5 | 5 | 5 |
| 121 | 5 | 5 | 4 |
| 123 | 5 | 5 | 5 |
| 126 | 5 | 5 | 4 |
| 127 | 5 | 5 | 5 |
| 129 | 5 | 5 | 5 |
| 131 | 5 | 5 | 5 |
| 134 | 5 | 5 | 5 |
| 135 | 5 | 5 | 5 |
| 137 | 5 | 5 | 3 |
| 139 | 5 | 5 | 5 |
| 143 | 5 | 5 | 5 |
| 144 | 5 | 5 | 5 |
| 145 | 5 | 5 | 5 |
| 147 | 5 | 5 | 5 |
| 148 | 5 | 5 | 5 |
| 150 | 5 | 5 | 5 |

TABLE 6-continued

| Compound No. | Herbicidal effect | | |
| --- | --- | --- | --- |
|  | Ec | Mo | Sc |
| 156 | 5 | 5 | 5 |
| 158 | 5 | 5 | 3 |
| 159 | 5 | 5 | 5 |
| 161 | 5 | 5 | 5 |
| 165 | 5 | 5 | 4 |
| 167 | 5 | 5 | 5 |
| 168 | 5 | 5 | 5 |
| 170 | 5 | 5 | 5 |
| 171 | 5 | 5 | 5 |
| (A) | 2 | 3 | 1 |
| (B) | 4 | 2 | 3 |

TEST EXAMPLE 2

(Herbicidal effect test by upland field soil treatment)

In a plastic pot (surface area: 120 $cm^2$) filled with upland field soil, barnyardgrass (Ec), pale smartweed (Po), slender amaranth (Am), common lambsquarters (Ch) and rice flatsedge (Ci) were-sown and covered with soil. A wettable powder prepared in accordance with Formulation Example 1 was diluted with water, and applied uniformly to the soil surface by a small-sized sprayer in an amount of 100 1/10 ares so as to apply 100 g of the active ingredient per 10 ares. The plants were then cultured in a green house, and the evaluation of the herbicidal effect was conducted on the 21th day after the treatment in accordance with the standard as identified in the above Table 5. The results are shown in the following Table 7.

TABLE 7

| Compound No. | Herbicidal effect | | | | |
| --- | --- | --- | --- | --- | --- |
|  | Ec | Po | Am | Ch | Ci |
| 2 | 2 | 4 | 5 | 5 | 4 |
| 4 | 4 | 4 | 5 | 5 | 5 |
| 7 | 5 | 5 | 5 | 5 | 5 |
| 11 | 4 | 4 | 5 | 4 | 4 |
| 16 | 3 | 5 | 5 | 4 | 3 |
| 20 | 4 | 5 | 5 | 5 | 4 |
| 22 | 5 | 5 | 5 | 5 | 5 |
| 23 | 5 | 5 | 5 | 5 | 5 |
| 25 | 5 | 5 | 5 | 5 | 5 |
| 47 | 5 | 5 | 5 | 5 | 5 |
| 49 | 5 | 5 | 5 | 5 | 5 |
| 86 | 5 | 5 | 5 | 5 | 5 |
| 87 | 5 | 5 | 5 | 5 | 5 |
| 88 | 5 | 5 | 5 | 5 | 5 |
| 89 | 5 | 5 | 5 | 5 | 5 |
| 90 | 5 | 5 | 5 | 5 | 5 |
| 91 | 5 | 5 | 5 | 5 | 5 |
| 94 | 5 | 5 | 5 | 5 | 5 |
| 100 | 5 | 5 | 5 | 5 | 5 |
| 102 | 5 | 5 | 5 | 5 | 5 |
| 104 | 5 | 5 | 5 | 5 | 5 |
| 105 | 5 | 5 | 5 | 5 | 5 |
| 106 | 5 | 5 | 5 | 5 | 5 |
| 109 | 5 | 5 | 5 | 5 | 5 |
| 113 | 5 | 5 | 5 | 5 | 5 |
| 115 | 5 | 5 | 5 | 5 | 5 |
| 119 | 4 | 5 | 5 | 5 | 5 |
| 121 | 5 | 5 | 5 | 5 | 5 |
| 123 | 4 | 5 | 5 | 5 | 5 |
| 129 | 4 | 5 | 5 | 5 | 5 |
| 131 | 5 | 5 | 5 | 5 | 5 |
| 134 | 5 | 5 | 5 | 5 | 5 |
| 135 | 5 | 5 | 5 | 5 | 5 |
| 137 | 4 | 5 | 5 | 5 | 5 |
| 139 | 5 | 5 | 5 | 5 | 5 |
| 143 | 4 | 5 | 5 | 5 | 5 |
| 145 | 4 | 5 | 5 | 5 | 5 |
| 147 | 5 | 5 | 5 | 5 | 5 |
| 148 | 5 | 5 | 5 | 5 | 5 |
| 150 | 4 | 5 | 5 | 5 | 5 |

TABLE 7-continued

| Compound No. | Herbicidal effect | | | | |
|---|---|---|---|---|---|
| | Ec | Po | Am | Ch | Ci |
| 152 | 4 | 5 | 5 | 5 | 4 |
| 154 | 4 | 5 | 5 | 5 | 5 |
| 156 | 5 | 5 | 5 | 5 | 5 |
| 158 | 5 | 5 | 5 | 5 | 5 |
| 159 | 5 | 5 | 5 | 5 | 5 |
| (A) | 0 | 0 | 2 | 2 | 4 |
| (B) | 1 | 0 | 0 | 1 | 0 |

TEST EXAMPLE 3

(Herbicidal effect test by upland field foliage treatment)

In a plastic pot (surface area: 120 cm$^2$) filled with upland field soil, barnyardgrass (Ec), pale smartweed (Po), slender amaranth (Am), common lambsquarters (Ch) and rice flatsedge (Ci) were sown and covered with soil and were cultured in a green house for 2 weeks. A wettable powder prepared in accordance with Formulation Example 1 was diluted with water, and applied onto the foliages by a small-sized sprayer in an amount of 100 l/10 ares so as to apply 100 g of the active ingredient per 10 ares. The plants were then cultured in the green house, and the evaluation of the herbicidal effect was conducted on the 14th day after the treatment in accordance with the standard as identified in the above Table 5. The results are shown in the following Table 8.

TABLE 8

| Compound No. | Herbicidal effect | | | | |
|---|---|---|---|---|---|
| | Ec | Po | Am | Ch | Ci |
| 1 | 1 | 5 | 5 | 5 | 4 |
| 2 | 4 | 5 | 5 | 5 | 5 |
| 4 | 4 | 5 | 5 | 5 | 5 |
| 7 | 5 | 5 | 5 | 5 | 5 |
| 11 | 4 | 4 | 4 | 5 | 5 |
| 20 | 3 | 4 | 5 | 5 | 4 |
| 22 | 4 | 4 | 5 | 5 | 4 |
| 23 | 5 | 5 | 5 | 5 | 5 |
| 25 | 5 | 5 | 5 | 5 | 5 |
| 47 | 5 | 5 | 5 | 5 | 5 |
| 49 | 5 | 5 | 5 | 5 | 5 |
| 52 | 3 | 4 | 5 | 5 | 5 |
| 86 | 5 | 5 | 5 | 5 | 5 |
| 87 | 5 | 5 | 5 | 5 | 5 |
| 88 | 5 | 5 | 5 | 5 | 5 |
| 89 | 5 | 5 | 5 | 5 | 5 |
| 90 | 5 | 5 | 5 | 5 | 5 |
| 91 | 5 | 5 | 5 | 5 | 5 |
| 94 | 4 | 5 | 5 | 5 | 5 |
| 100 | 5 | 5 | 5 | 4 | 4 |
| 102 | 5 | 5 | 5 | 5 | 5 |
| 104 | 5 | 5 | 5 | 5 | 5 |
| 106 | 5 | 5 | 5 | 5 | 5 |
| 107 | 4 | 5 | 5 | 5 | 4 |
| 109 | 5 | 5 | 5 | 5 | 5 |
| 113 | 5 | 5 | 5 | 5 | 5 |
| 115 | 5 | 5 | 5 | 5 | 4 |
| 119 | 4 | 5 | 5 | 4 | 5 |
| 121 | 5 | 5 | 5 | 4 | 4 |
| 123 | 5 | 5 | 5 | 4 | 4 |
| 126 | 4 | 5 | 5 | 4 | 5 |
| 129 | 5 | 5 | 5 | 5 | 5 |
| 131 | 5 | 5 | 5 | 5 | 5 |
| 132 | 4 | 5 | 5 | 4 | 5 |
| 134 | 4 | 5 | 5 | 5 | 5 |
| 135 | 4 | 5 | 5 | 5 | 4 |
| 139 | 5 | 5 | 5 | 5 | 5 |
| 143 | 4 | 5 | 5 | 4 | 4 |
| 147 | 5 | 5 | 5 | 5 | 5 |
| 148 | 5 | 5 | 5 | 5 | 5 |
| 156 | 4 | 5 | 5 | 5 | 5 |
| 158 | 4 | 5 | 5 | 5 | 3 |
| 159 | 4 | 5 | 5 | 5 | 3 |

TABLE 8-continued

| Compound No. | Herbicidal effect | | | | |
|---|---|---|---|---|---|
| | Ec | Po | Am | Ch | Ci |
| 161 | 5 | 5 | 5 | 5 | 5 |
| 162 | 4 | 5 | 5 | 5 | 4 |
| 163 | 5 | 5 | 5 | 5 | 5 |
| (A) | 0 | 1 | 2 | 2 | 3 |
| (B) | 0 | 0 | 0 | 1 | 3 |

TEST EXAMPLE 4

(Herbicidal effect test and phytotoxicity test to rice by upland field foliage treatment)

In a plastic pot (surface area: 600 cm$^2$) filled with upland field soil, rice (Or), johnsongrass (So), Alopecurus aequalis (Al), pale smartweed (Po), slender amaranth (Am) and common lambsquarters (Ch) were sown and covered with soil, and were cultured in a green house for 2 weeks. A predetermined amount of a wettable powder prepared in accordance with Formulation Example 1 was diluted with 100 l of water per 10 ares, and was applied onto the foliages by a small-sized sprayer. The plants were then cultured in the green house, and the evaluation of the herbicidal effect and the phytotoxicity was conducted on the 14th day after the treatment in accordance with the standard as identified in the above Table 5. The results are shown in the following Table 9. The dose of active ingredient in the Table shows the amount of the active ingredient (g) per 10 ares.

TABLE 9

| Compound No. | Dose of active ingredient | Phytotoxicity Or | Herbicidal effect | | | | |
|---|---|---|---|---|---|---|---|
| | | | So | Al | Po | Am | Ch |
| 113 | 6.3 | 1 | 5 | 5 | 5 | 5 | 4 |
| 115 | 6.3 | 0 | 5 | 5 | 5 | 5 | 4 |
| 135 | 6.3 | 1 | 5 | 5 | 5 | 5 | 5 |
| 137 | 6.3 | 0 | 4 | 3 | 4 | 4 | 4 |
| 142 | 25.0 | 1 | 4 | 4 | 5 | 5 | 5 |
| A | 25.0 | 0 | 0 | 0 | 0 | 0 | 0 |
| B | 25.0 | 0 | 0 | 0 | 0 | 0 | 0 |

TEST EXAMPLE 5

(Herbicidal effect test and phytotoxicity test to rice by upland field soil treatment)

In a plastic pot (surface area: 600 cm$^2$) filled with upland field soil, rice (Or), johnsongrass (So), Alopecurus aequalis (Al), pale smartweed (Po), slender amaranth (Am) and common lambsquarters (Ch) were sown and covered with soil. After absorbing water from the bottom of the pot, a predetermined amount of a wettable powder prepared in accordance with Formulation Example 1 was diluted with 100 l of water per 10 ares, and was applied onto the soil surface by a small-sized sprayer. The plants were then cultured again in a green house, and the evaluation of the herbicidal effect and the phytotoxicity was conducted on the 20th day after the treatment in accordance with the standard as identified in the above Table 5. The results are shown in the following Table 10. The dose of active ingredient in the Table shows the amount of the active ingredient (g) per 10 ares.

TABLE 10

| Compound No. | Dose of active ingredient | Phytotoxicity Or | Herbicidal effect | | | | |
|---|---|---|---|---|---|---|---|
| | | | So | Al | Po | Am | Ch |
| 87 | 1.6 | 1 | 5 | 5 | 5 | 5 | 5 |
| 88 | 1.6 | 0 | 5 | 4 | 5 | 5 | 3 |
| 89 | 1.6 | 1 | 5 | 5 | 5 | 5 | 3 |
| 90 | 1.6 | 0 | 5 | 3 | 4 | 5 | 3 |
| 94 | 6.3 | 0 | 5 | 5 | 5 | 5 | 5 |
| 132 | 6.3 | 1 | 5 | 3 | 5 | 5 | 4 |
| 142 | 25.0 | 1 | 3 | 3 | 5 | 5 | 5 |
| 150 | 1.6 | 0 | 3 | 3 | 5 | 5 | 5 |
| A | 25.0 | 0 | 0 | 0 | 0 | 0 | 0 |
| B | 25.0 | 0 | 0 | 0 | 0 | 0 | 0 |

TEST EXAMPLE 6

(Herbicidal effect test and phytotoxicity test to wheat by upland field foliage treatment)

In a plastic pot (surface area: 600 cm$^2$) filled with upland field soil, wheat (Tr), johnsongrass (So), Alopecurus aequalis (Al), pale smartweed (Po), slender amaranth (Am) and common lambsquarters (Ch) were sown and covered with soil, and were cultured in a green house for 2 weeks. A predetermined amount of a wettable powder prepared in accordance with Formulation Example 1 was diluted with 100 l of water per 10 ares, and was applied onto the foliages by a small-sized sprayer. The plants were then cultured again in a green house, and the evaluation of the herbicidal effect and the phytotoxicity was conducted on the 14th day after the treatment in accordance with the standard as identified in the above Table 5. The results are shown in the following Table 11. The dose of active ingredient in the Table shows the amount of the active ingredient (g) per 10 ares.

TABLE 11

| Compound No. | Dose of active ingredient | Phytotoxicity Tr | Herbicidal effect | | | | |
|---|---|---|---|---|---|---|---|
| | | | So | Al | Po | Am | Ch |
| 94 | 6.3 | 0 | 5 | 5 | 5 | 5 | 5 |
| 104 | 1.6 | 1 | 5 | 5 | 5 | 5 | 4 |
| 109 | 25.0 | 0 | 4 | 4 | 5 | 5 | 5 |
| 113 | 6.3 | 0 | 5 | 5 | 5 | 5 | 4 |
| 115 | 6.3 | 0 | 5 | 5 | 5 | 5 | 4 |
| 131 | 6.3 | 1 | 5 | 5 | 5 | 5 | 5 |
| 134 | 6.3 | 1 | 5 | 5 | 5 | 5 | 5 |
| 135 | 6.3 | 1 | 5 | 5 | 5 | 5 | 5 |
| 137 | 6.3 | 0 | 4 | 3 | 4 | 4 | 4 |
| 143 | 25.0 | 1 | 5 | 5 | 5 | 4 | 4 |
| A | 25.0 | 0 | 0 | 0 | 0 | 0 | 0 |
| B | 25.0 | 0 | 0 | 0 | 0 | 0 | 0 |

TEST EXAMPLE 7

(Herbicidal effect test and phytotoxicity test to wheat by upland field soil treatment)

In a plastic pot (surface area: 600 cm$^2$) filled with upland field soil, wheat (Tr), johnsongrass (So), Alopecurus aequalis (Al), pale smartweed (Po), slender amaranth (Am) and common lambsquarters (Ch) were sown and covered with soil. After absorbing water from the bottom of the pot, a predetermined amount of a wettable powder prepared in accordance with Formulation Example 1 was diluted with 100 l of water per 10 ares, and was applied onto the soil surface by a small-sized sprayer. The plants were then cultured again in a green house, and the evaluation of the herbicidal effect and the phytotoxicity was conducted on the 20th day after the treatment in accordance with the standard as identified in the above Table 5. The results are shown in the following Table 12. The dose of active ingredient in the Table shows the amount of the active ingredient (g) per 10 ares.

TABLE 12

| Compound No. | Dose of active ingredient | Phytotoxicity Tr | Herbicidal effect | | | | |
|---|---|---|---|---|---|---|---|
| | | | So | Al | Po | Am | Ch |
| 88 | 1.6 | 0 | 5 | 4 | 5 | 5 | 3 |
| 89 | 1.6 | 0 | 5 | 5 | 5 | 5 | 3 |
| 90 | 1.6 | 0 | 5 | 5 | 5 | 5 | 3 |
| 94 | 6.3 | 0 | 5 | 5 | 5 | 5 | 5 |
| 109 | 6.3 | 1 | 5 | 5 | 4 | 5 | 5 |
| 115 | 25.0 | 1 | 5 | 5 | 5 | 5 | 5 |
| 129 | 6.3 | 0 | 5 | 5 | 5 | 5 | 5 |
| 131 | 1.6 | 0 | 5 | 5 | 5 | 5 | 5 |
| 132 | 6.3 | 0 | 5 | 3 | 5 | 5 | 4 |
| 135 | 6.3 | 1 | 5 | 5 | 5 | 5 | 5 |
| 137 | 6.3 | 0 | 5 | 5 | 5 | 5 | 5 |
| 142 | 25.0 | 1 | 3 | 3 | 5 | 5 | 5 |
| 143 | 25.0 | 1 | 5 | 5 | 5 | 5 | 3 |
| 150 | 1.6 | 0 | 3 | 3 | 5 | 5 | 5 |
| A | 25.0 | 0 | 0 | 0 | 0 | 0 | 0 |
| B | 25.0 | 0 | 0 | 0 | 0 | 0 | 0 |

TEST EXAMPLE 8

(Herbicidal effect test and phytotoxicity test to the cotton by upland field foliage treatment)

In a plastic pot (surface area: 600 cm$^2$) filled with upland field soil, cotton (Go), johnsongrass (So), Alopecurus aequalis (Al), pale smartweed (Po), slender amaranth (Am) and common lambsquarters (Ch) were sown and covered with soil, and were cultured in a green house for 2 weeks. A predetermined amount of a wettable powder prepared in accordance with Formulation Example 1 was diluted with 100 l of water per 10 ares, and was applied onto the foliage by a small-sized sprayer. The plants were then cultured in the green house, and the evaluation of the herbicidal effect and the phytotoxicity was conducted on the 14th day after the treatment in accordance with the standard as identified in the above Table 5. The results are shown in the following Table 13. The dose of active ingredient in the Table shows the amount of the active ingredient (g) per 10 ares.

TABLE 13

| Compound No. | Dose of active ingredient | Phytotoxicity Go | Herbicidal effect | | | | |
|---|---|---|---|---|---|---|---|
| | | | So | Al | Po | Am | Ch |
| 104 | 1.6 | 1 | 5 | 5 | 5 | 5 | 4 |
| 142 | 25.0 | 1 | 4 | 4 | 5 | 5 | 5 |
| A | 100.0 | 2 | 0 | 0 | 2 | 3 | 2 |
| B | 400.0 | 2 | 0 | 0 | 0 | 2 | 1 |

TEST EXAMPLE 9

(Herbicidal effect test and phytotoxicity test to cotton by upland field soil treatment)

In a plastic pot (surface area: 600 cm$^2$) filled with upland field soil, cotton (Go), johnsongrass (So), Alopecurus aequalis (Al), pale smartweed (Po), slender amaranth (Am) and common lambsquarters (Ch) were sown and covered with soil. After absorbing water from the bottom of the pot, a predetermined amount of a wettable powder prepared in accordance with Formulation Example 1 was diluted with 100 l of water per 10 ares, and was applied onto the soil surface by a small-sized sprayer. The plants were then cultured again in a green house, and the evaluation of the herbicidal effect and the phytotoxicity was conducted on the 20th day after the treatment in accordance with the standard as identified in the above Table 5. The results are shown in the following Table 14. The dose of active ingredient in the Table shows the amount of the active ingredient (g) per 10 ares.

TABLE 14

| Compound No. | Dose of active ingredient | Phytotoxicity Go | Herbicidal effect | | | | |
|---|---|---|---|---|---|---|---|
| | | | So | Al | Po | Am | Ch |
| 87 | 1.6 | 0 | 5 | 5 | 5 | 5 | 5 |
| 88 | 1.6 | 1 | 5 | 4 | 5 | 5 | 3 |
| 89 | 1.6 | 1 | 5 | 5 | 5 | 5 | 3 |
| 90 | 1.6 | 1 | 5 | 3 | 4 | 5 | 3 |
| 106 | 6.3 | 1 | 3 | 5 | 5 | 5 | 5 |
| 115 | 25.0 | 1 | 5 | 5 | 5 | 5 | 5 |
| 131 | 1.6 | 0 | 5 | 5 | 5 | 5 | 5 |
| 142 | 25.0 | 0 | 3 | 3 | 5 | 5 | 5 |
| A | 400.0 | 2 | 0 | 0 | 1 | 4 | 2 |
| B | 400.0 | 2 | 1 | 0 | 0 | 3 | 2 |

We claim:

1. A compound having the following formula or a herbicidally acceptable salt thereof:

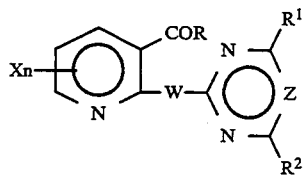

wherein R is selected from the group consisting of a hydrogen atom, a hydroxyl group, a $C_1-C_7$ alkoxy group, a $C_1-C_7$ alkoxy $C_1-C_7$ alkoxy group, a pivaloyloxymethoxy group, a benzyloxy group, a benzyloxy group substituted with a chlorine atom or a methoxy group, a trimethylsilylethoxy group, a methylsulfonylamino group, a methylthio group, a phenoxy group and a phenylthio group;

$R^1$ and $R^2$ which are the same or different, are selected from the group consisting of a hydrogen atom, a $C_1-C_7$ alkoxy group, a halogen atom, a $C_1-C_3$ alkylamino group, a di $C_1-C_3$ alkylamino group, a halo $C_1-C_7$ alkoxy group and a $C_1-C_7$ alkyl group;

W is an oxygen atom a NH group or a group of the formula, >NC(O)B, wherein B is a hydrogen atom or a $C_1-C_7$ alkoxy group;

Z is a methine group;

X is selected from the group consisting of a phenyl group, a phenyl group substituted with a substituent selected from the group consisting of a $C_1-C_7$ alkyl group, a halogen atom, a nitro group, a halo $C_1-C_3$ alkyl group, a halo $C_1-C_7$ alkoxy group, a $C_1-C_7$ alkoxy group, a piperidino group, a di $C_1-C_3$ alkylamino group, a phenoxy group, a methylphenoxy group, an ethoxymethoxy group, a methoxyethoxy group, a methoxymethyl group, a cyano group, an ethynyl group, a $C_1-C_3$ alkylamino group, an ethoxycarbonyl $C_1-C_2$ alkoxy group, a methoxymethyl group, a methylthiomethoxy group, a methylthioethoxy group, an ethylthiomethoxy group, a benzyloxy group, and a hydroxyl group and a group having the formula;

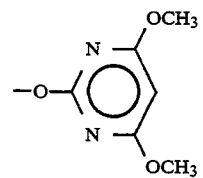

and n is an integer of 1 to 3, and X may be a combination of different groups when n is at least 2.

2. A herbicidal composition comprising a herbicidally effective amount of the compound or the salt thereof as defined in claim 1 and an agriculturally acceptable adjuvant.

3. A method for killing weeds which comprises applying an herbicidally effective amount of the compound or the salt thereof as defined in claim 1 to a locus to be protected.

4. A compound having the following formula or a herbicidally acceptable salt thereof:

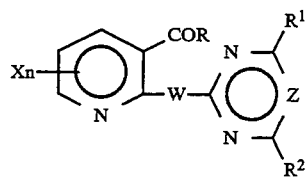

wherein R is selected from the group consisting of a hydrogen atom, a hydroxyl group, a $C_1-C_7$ alkoxy $C_1-C_7$ alkoxy group, a pivaloyloxymethoxy group, a benzyloxy group, a benzyloxy group substituted with a chlorine atom or a methoxy group, a trimethylsilylethoxy group, a methylsulfonylamino group, a methylthio group, a phenoxy group, a phenythio group and an imidazolyl group;

$R^1$ and $R^2$ which are the same or different, are selected from the group consisting of a hydrogen atom, a $C_1-C_7$ alkoxy group, a halogen atom, a $C_1-C_3$ alkylamino group, a di $C_1-C_3$ alkylamino group, a halo $C_1-C_7$ alkoxy group and a $C_1-C_7$ alkyl group;

W is an oxygen atom, a NH group or a group of the formula, >NC(O)B, wherein B is a hydrogen atom or a $C_1-C_7$ alkoxy group;

Z is a methine group;

X is selected from the group consisting of a phenyl group, a phenyl group substituted with a substituent selected from the group consisting of a $C_1-C_7$ alkyl group, a halogen atom, a nitro group, a halo $C_1-C_3$ alkyl group, a halo $C_1-C_7$ alkoxy group, a $C_1-C_7$ alkoxy group, a piperidino group, a di $C_1-C_3$ alkylamino group, a phenoxy group, a methylphenoxy group, an ethoxymethoxy group, a methoxyethoxy group, a methoxymethoxy group, a cyano group, an ethynyl group, a $C_1-C_3$ alkylamino group, an ethoxycarbonyl $C_1-C_2$ alkoxy group, a methoxymethyl group, a methylthiomethoxy group, a methylthioethoxy group, an ethylthiomethoxy group, a benzyloxy group, and a hydroxyl group and a group having the formula;

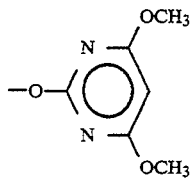

and n is an integer of 1 to 3, and X may be a combination of different groups when n is at least 2.

5. The pyridine derivative or its salt according to claim 1, wherein R is selected from the group consisting of a hydrogen atom, a hydroxyl group, a $C_1$-$C_7$ alkoxy group, a benzyloxy group or a trimethylsilylethoxy group;

R$^1$ and R$^2$ which are the same or different, are selected from the group consisting of a hydrogen atom, a $C_1$-$C_7$ alkoxy group, a halogen atom, a $C_1$-$C_3$ alkylamino group, a halo $C_1$-$C_7$ alkoxy group and a $C_1$-$C_7$ alkyl group;

X is a phenyl group;

W is an oxygen atom or a NH group.

6. The pyridine derivative or its salt according to claim 1, wherein R is selected from the group consisting of a hydrogen atom, a hydroxyl group, a $C_1$-$C_7$ alkoxy group, a $C_1$-$C_7$ alkoxy $C_1$-$C_7$ alkoxy group, a pivaloyloxymethyl group, a benzyloxy group, a trimethylsilylethoxy group, a methylsulfonylamino group, a methylthio group, a phenoxy group, and a phenylthio group;

R$^1$ and R$^2$ which are the same or different, are selected from the group consisting of a hydrogen atom, a $C_1$-$C_7$ alkoxy group, a halogen atom, a $C_1$-$C_3$ alkylamino group, a di $C_1$-$C_3$ alkylamino group, a halo $C_1$-$C_7$ alkoxy group and a $C_1$-$C_7$ alkyl group;

X is a group of the formula;

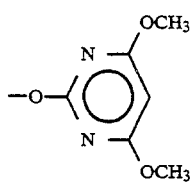

and n is an integer of 1 to 3.

7. A compound having the following formula or a herbicidally acceptable salt thereof:

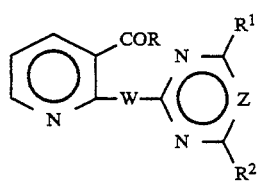

wherein R is selected from the group consisting of a hydrogen atom, a hydroxyl group, a $C_1$-$C_7$ alkoxy group, a $C_1$-$C_7$ alkoxy $C_1$-$C_7$ alkoxy group, a pivaloyloxymethoxy group, a benzyloxy group, a benzyloxy group substituted with a chlorine atom or a methoxy group, a trimethylsilylethoxy group, a methylsulfonylamino group, a methylthio group, a phenoxy group and a phenylthio group;

R$^1$ and R$^2$ which are the same or different, are selected from the group consisting of a hydrogen atom, a $C_1$-$C_7$ alkoxy group, a halogen atom, a $C_1$-$C_3$ alkylamino group, a di $C_1$-$C_3$ alkylamino group, a halo $C_1$-$C_7$ alkoxy group and a $C_1$-$C_7$ alkyl group;

W is a NH group or a group of the formula, >NC(O)B, wherein B is a hydrogen atom or a $C_1$-$C_7$ alkoxy group; and Z is a methine group.

8. A pyridine derivative having the following general formula or its salt:

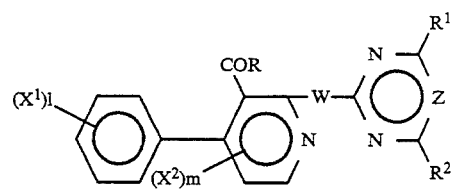

wherein R is selected from the group consisting of a hydrogen atom, a hydroxyl group, a $C_1$-$C_7$ alkoxy group, a $C_1$-$C_7$ alkoxy $C_1$-$C_7$ alkoxy group, a pivaloyloxymethoxy group, a benzyloxy group, a benzyloxy group substituted with a chlorine atom or a methoxy group, a trimethylsilylethoxy group, a methylsulfonylamino group, a methylthio group, a phenoxy group and a phenythio group;

R$^1$ and R$^2$ which are the same or different, are selected from the group consisting of a hydrogen atom, a $C_1$-$C_7$ alkoxy group, a halogen atom, a $C_1$-$C_3$ alkylamino group, a di $C_1$-$C_3$ alkylamino group, a halo $C_1$-$C_7$ alkoxy group and a $C_1$-$C_7$ alkyl group;

W is an oxygen atom;

Z is a methine group;

X$^1$ is selected from the group consisting of a halogen atom, a $C_1$-$C_7$ alkyl group, a $C_1$-$C_7$ alkoxy group, a $C_1$-$C_3$ alkylamino group, a di $C_1$-$C_7$ alkylamino group, a halo $C_1$-$C_3$ alkyl group, a halo $C_1$-$C_7$ alkoxy group, a nitro group, a hydroxyl group, a $C_1$-$C_7$ alkoxy $C_1$-$C_7$ alkoxy group, an ethoxycarbonyl $C_1$-$C_2$ alkoxy group, a methylthiomethoxy group, a methylthioethoxy group, an ethylthiomethoxy group, a benzyloxy group, a cyano group, a phenoxy group, a methylthio group, a methoxymethyl group and an ethynyl group;

X$^2$ is selected from the group consisting of a halogen atom, a $C_1$-$C_2$ alkyl group, a methoxy group and a dimethylamino group;

l is 0 or an integer of 1 to 3, and X$^1$ can be a combination of different groups when l is at least 2; and m is 0 or an integer of 1 or 2, and X$^2$ can be a combination of different groups when m is at least 2.

9. A pyridine derivative having the following general formula or its salt:

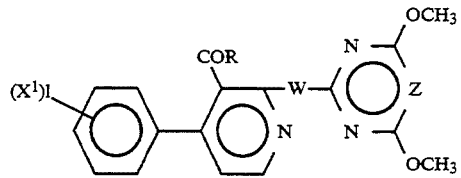

wherein R is selected from the group consisting of a hydroxyl group, a $C_1$-$C_7$ alkoxy group, a $C_1$-$C_7$ alkoxy $C_1$-$C_7$ alkoxy group, a pivaloyloxymethoxy group, a benzyloxy group, a benzyloxy group substituted with a chlorine atom or a methoxy group, a trimethylsilylmethoxy group, a methylsulfonylamino group, a methylthio group, and a phenoxy group;

W is an oxygen;

Z is a methine group;

$X^1$ is selected from the group consisting of a halogen atom, a $C_1$-$C_7$ alkyl group, a $C_1$-$C_7$ alkoxy group, a $C_1$-$C_3$ alkylamino group, a di $C_1$-$C_3$ alkylamino group, a halo $C_1$-$C_3$ alkyl group, a halo $C_1$-$C_7$ alkoxy group, a nitro group, a hydroxyl group, a $C_1$-$C_7$ alkoxy $C_1$-$C_7$ alkoxy group, an ethoxycarbonyl $C_1$-$C_2$ alkoxy group, a methylthiomethoxy group, a methylthioethoxy group, an ethylthiomethoxy group, a benzyloxy group, a cyano group, a phenoxy group, a methylthio group, a methoxymethyl group and an ethynyl group;

l is 0 or an integer of 1 to 3, and $X^1$ can be a combination of different groups when l is at least 2.

* * * * *